(12) United States Patent
Hazen et al.

(10) Patent No.: US 8,722,344 B2
(45) Date of Patent: May 13, 2014

(54) RISK MARKERS FOR CARDIOVASCULAR DISEASE

(71) Applicants: Stanley L. Hazen, Pepper Pike, OH (US); Michael Kinter, Shaker Heights, OH (US); Marc S. Penn, Beachwood, OH (US); Jonathan Smith, Shaker Heights, OH (US); Lemin Zheng, Cleveland, OH (US)

(72) Inventors: Stanley L. Hazen, Pepper Pike, OH (US); Michael Kinter, Shaker Heights, OH (US); Marc S. Penn, Beachwood, OH (US); Jonathan Smith, Shaker Heights, OH (US); Lemin Zheng, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/683,527

(22) Filed: Nov. 21, 2012

(65) Prior Publication Data

US 2013/0177551 A1    Jul. 11, 2013

Related U.S. Application Data

(60) Division of application No. 12/730,137, filed on Mar. 23, 2010, now Pat. No. 8,338,110, which is a continuation of application No. 11/005,563, filed on Dec. 6, 2004, now Pat. No. 7,781,219.

(60) Provisional application No. 60/527,178, filed on Dec. 5, 2013, provisional application No. 60/600,527, filed on Aug. 11, 2004, provisional application No. 60/600,551, filed on Aug. 11, 2004, provisional application No. 60/619,044, filed on Oct. 15, 2004.

(51) Int. Cl.
*G01N 33/53* (2006.01)

(52) U.S. Cl.
USPC ............................................ 435/7.1; 436/518

(58) Field of Classification Search
None
See application file for complete search history.

(56) References Cited

PUBLICATIONS

Lawler et al. (Int. J. Sports Med. 2002 vol. 23, p. 477-483).*

* cited by examiner

*Primary Examiner* — Jacob Cheu
(74) *Attorney, Agent, or Firm* — Tarolli, Sundheim, Covell & Tummino LLP

(57) ABSTRACT

Provided herein methods for determining whether a subject, particularly a human subject, is at risk of developing, having, or experiencing a complication of cardiovascular disease, and methods of treating subjects who are identified by the current methods of being at risk for cardiovascular disease. In one embodiment, the method comprises determining levels of one or more oxidized apolipoprotien A-I related biomolecules in a bodily sample from the subject. Also, provided are kits and reagents for use in the present methods. Also provided are methods for monitoring the status of cardiovascular disease in a subject or the effects of therapeutic agents on subjects with cardiovascular disease. Such method comprising determining levels of one or more oxidized apolipoprotein A-I related molecules in bodily samples taken from the subject over time or before and after therapy.

9 Claims, 11 Drawing Sheets

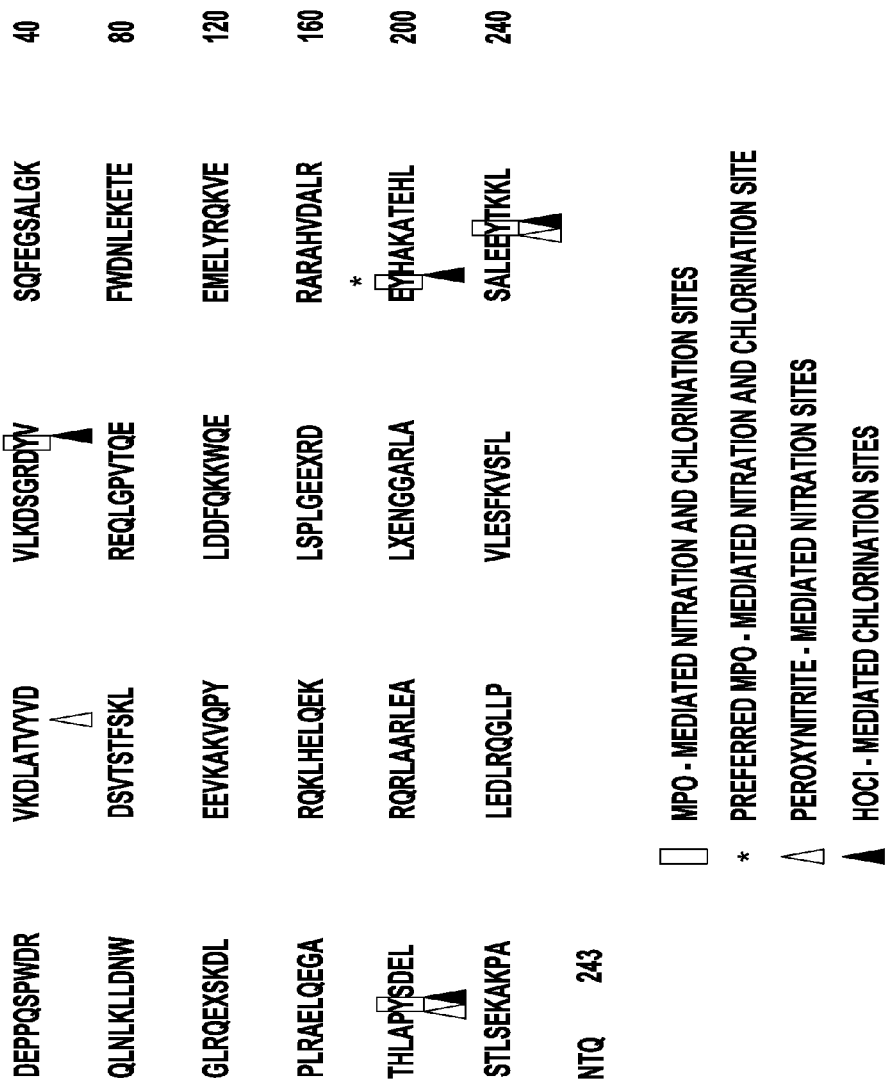

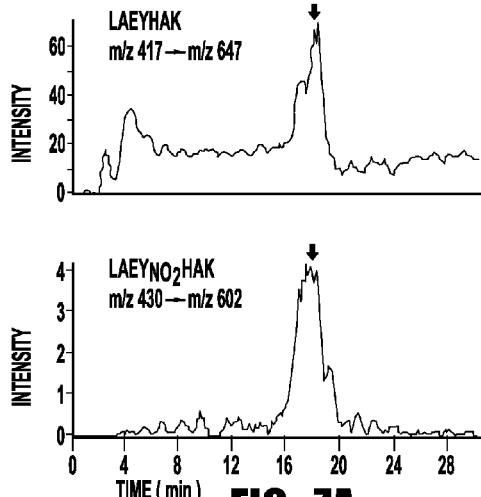
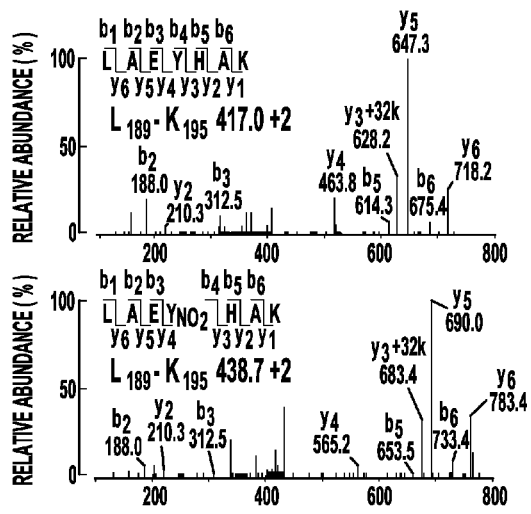
FIG. 7A
FIG. 7B
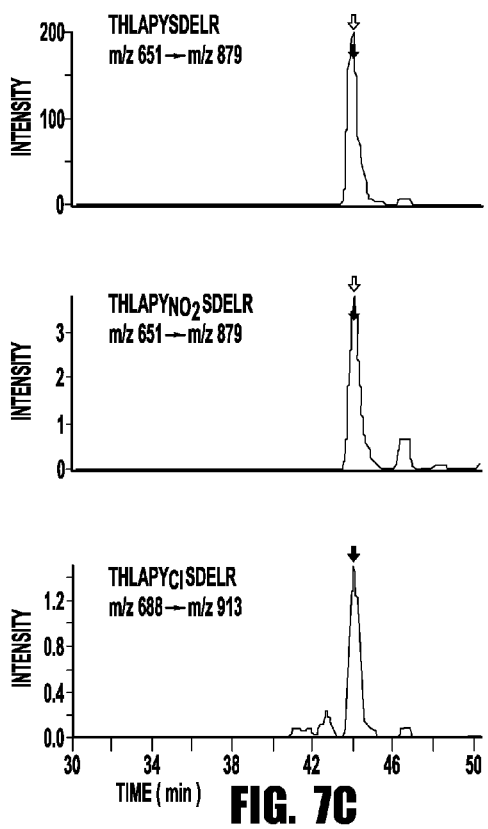
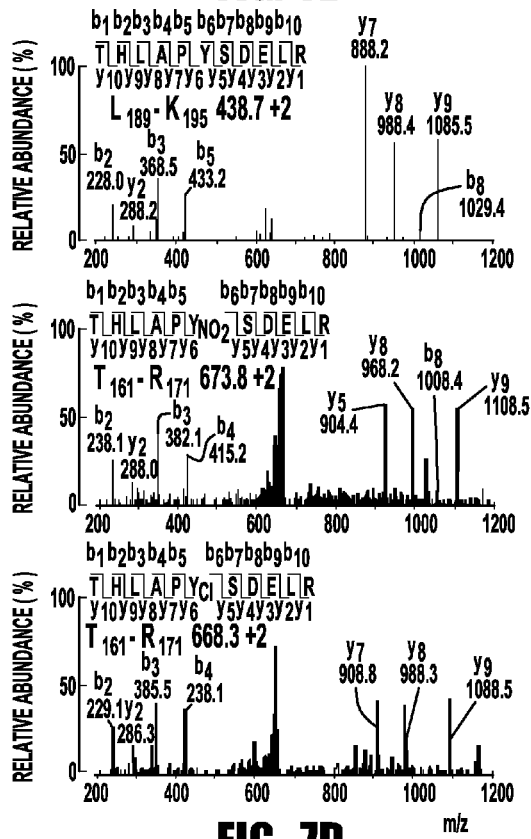
FIG. 7C
FIG. 7D

SEQUENCE LISTING

```
<160> NUMBER OF SEQ ID NOS: 14

<210> SEQ ID NO 1
<211> LENGTH: 243
<212> TYPE: PRT
<213> ORGANISM: Homo sapiens

<400> SEQUENCE: 1

Asp Glu Pro Pro Gln Ser Pro Trp Asp Arg Val Lys Asp Leu Ala Thr
 1               5                  10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
 65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 2
<211> LENGTH: 13
<212> TYPE: PRT
<213> ORGANISM: Homo sapiens

<400> SEQUENCE: 2

Asp Tyr Val Ser Gln Phe Glu Gly Ser Ala Leu Ala Leu
 1               5                  10
```

-continued

<210> SEQ ID NO 3
<211> LENGTH: 13
<212> TYPE: PRT
<213> ORGANISM: Homo sapiens

<400> SEQUENCE: 3

Asp Tyr Val Ser Gln Phe Glu Gly Ser Ala Leu Gly Lys
1               5                   10

<210> SEQ ID NO 4
<211> LENGTH: 7
<212> TYPE: PRT
<213> ORGANISM: Homo sapiens

<400> SEQUENCE: 4

Leu Ala Glu Tyr His Ala Lys
1               5

<210> SEQ ID NO 5
<211> LENGTH: 11
<212> TYPE: PRT
<213> ORGANISM: Homo sapiens

<400> SEQUENCE: 5

Thr His Leu Ala Pro Tyr Ser Asp Glu Leu Arg
1               5                   10

<210> SEQ ID NO 6
<211> LENGTH: 8
<212> TYPE: PRT
<213> ORGANISM: Homo sapiens

<400> SEQUENCE: 6

Asp Tyr Gly Ser Ala Leu Gly Lys
1               5

<210> SEQ ID NO 7
<211> LENGTH: 12
<212> TYPE: PRT
<213> ORGANISM: Homo sapiens

<400> SEQUENCE: 7

Val Ser Phe Leu Ser Ala Leu Glu Glu Tyr Thr Lys
1               5                   10

<210> SEQ ID NO 8
<211> LENGTH: 11
<212> TYPE: PRT
<213> ORGANISM: Homo sapiens

<400> SEQUENCE: 8

Asp Leu Ala Thr Val Tyr Val Asp Val Leu Lys
1               5                   10

<210> SEQ ID NO 9
<211> LENGTH: 11
<212> TYPE: PRT
<213> ORGANISM: Homo sapiens

<400> SEQUENCE: 9

Ala Thr Glu His Leu Ser Thr Leu Ser Glu Lys
1               5                   10

```
<210> SEQ ID NO 10
<211> LENGTH: 11
<212> TYPE: PRT
<213> ORGANISM: Homo sapiens

<400> SEQUENCE: 10

Gln Gly Leu Leu Pro Val Leu Glu Ser Phe Lys
 1               5                  10

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Cys Gly Tyr Gly Gly Gly Tyr Gly
 1               5

<210> SEQ ID NO 12
<211> LENGTH: 13
<212> TYPE: PRT
<213> ORGANISM: Homo sapiens
<220> FEATURE:
<221> NAME/KEY: MOD_RES
<222> LOCATION: (2)
<223> OTHER INFORMATION: Trihydroxyphenylalanine

<400> SEQUENCE: 12

Asp Xaa Val Ser Gln Phe Glu Gly Ser Ala Leu Gly Lys
 1               5                  10

<210> SEQ ID NO 13
<211> LENGTH: 13
<212> TYPE: PRT
<213> ORGANISM: Homo sapiens
<220> FEATURE:
<221> NAME/KEY: MOD_RES
<222> LOCATION: (6)
<223> OTHER INFORMATION: Dihydroxyphenylalanine

<400> SEQUENCE: 13

Asp Tyr Val Ser Gln Xaa Glu Gly Ser Ala Leu Gly Lys
 1               5                  10

<210> SEQ ID NO 14
<211> LENGTH: 11
<212> TYPE: PRT
<213> ORGANISM: Homo sapiens
<220> FEATURE:
<221> NAME/KEY: MOD_RES
<222> LOCATION: (6)
<223> OTHER INFORMATION: Trihydroxyphenylalanine

<400> SEQUENCE: 14

Thr His Leu Ala Pro Xaa Ser Asp Glu Leu Arg
 1               5                  10
```

RISK MARKERS FOR CARDIOVASCULAR DISEASE

CROSS-REFERENCE TO RELATED APPLICATIONS

This application is a divisional of U.S. application Ser. No. 12/730,137, which is a continuation of U.S. application Ser. No. 11/005,563, filed Dec. 6, 2004, which claims the benefit of U.S. Provisional Application No. 60/527,178, filed Dec. 5, 2003, U.S. Provisional Application No. 60/600,527, filed Aug. 11, 2004, U.S. Provisional Application No. 60/600,551, filed Aug. 11, 2004, and U.S. Provisional Application No. 60/619,044, filed Oct. 15, 2004, all of which are incorporated herein by reference in their entirety.

GOVERNMENT RIGHTS

The work described in this application was supported, at least in part, by Grant Nos. HL62526, HL076491, HL70621, HL077692, and HL66082. The United States government has certain rights in this invention.

FIELD OF THE INVENTION

The present invention relates to the field of cardiovascular disease. More specifically, it relates to markers and methods for determining whether a subject, particularly a human subject, is at risk of developing cardiovascular disease, having cardiovacular disease, or experiencing a complication of cardiovascular disease. The present application also relates to the use of such markers and methods for monitoring the status of cardiovascular disease in a subject or the effects of therapeutic agents on subjects with cardiovascular disease.

Cardiovascular disease (CVD) is the general term for heart and blood vessel diseases, including atherosclerosis, coronary heart disease, cerebrovascular disease, aorto-iliac disease, and peripheral vascular disease. Subjects with CVD may develop a number of complications, including, but not limited to, myocardial infarction, stroke, angina pectoris, transient ischemic attacks, congestive heart failure, aortic aneurysm and death. CVD accounts for one in every two deaths in the United States and is the number one killer disease. Thus, prevention of cardiovascular disease is an area of major public health importance.

A low-fat diet and exercise are recommended to prevent CVD. In addition, a number of therapeutic agents may be prescribed by medical professionals to those individuals who are known to be at risk for developing or having CVD. These include lipid-lowering agents that reduce blood levels of cholesterol and trigylcerides, agents that normalize blood pressure, agents, such as aspirin or platelet ADP receptor antagonist (e.g., clopidogrel and ticlopidine) that prevent activation of platelets and decrease vascular inflammation, and pleotrophic agents such as peroxisome proliferator activated receptor (PPAR) agonists, with broad-ranging metabolic effects that reduce inflammation, promote insulin sensitization, improve vascular function, and correct lipid abnormalities. More aggressive therapy, such as administration of multiple medications or surgical intervention may be used in those individuals who are at high risk. Since CVD therapies may have adverse side effects, it is desirable to have methods for identifying those individuals who are at risk, particularly those individuals who are at high risk, of developing or having CVD.

Currently, several risk factors are used by medical professionals to assess an individual's risk of developing or having CVD and to identify individuals at high risk. Major risk factors for cardiovascular disease include age, hypertension, family history of premature CVD, smoking, high total cholesterol, low HDL cholesterol, obesity and diabetes. The major risk factors for CVD are additive, and are typically used together by physicians in a risk prediction algorithm to target those individuals who are most likely to benefit from treatment for CVD. These algorithms achieve a high sensitivity and specificity for predicting risk of CVD within 10 years. However, the ability of the present algorithms to predict a higher probability of developing CVD is limited. Among those individuals with none of the current risk factors, the 10-year risk for developing CVD is still about 2%. In addition, a large number of CVD complications occur in individuals with apparently low to moderate risk profiles, as determined using currently known risk factors. Thus, there is a need to expand the present cardiovascular risk algorithm to identify a larger spectrum of individuals at risk for or affected with CVD.

The mechanism of atherosclerosis is not well understood. Over the past decade a wealth of clinical, pathological, biochemical and genetic data support the notion that atherosclerosis is a chronic inflammatory disorder. Acute phase reactants (e.g. C-reactive protein, complement proteins), sensitive but non-specific markers of inflammation, are enriched in fatty streaks and later stages of atherosclerotic lesions. In a recent prospective clinical trial, base-line plasma levels of C-reactive protein independently predicted risk of first-time myocardial infarction and stroke in apparently healthy individuals. U.S. Pat. No. 6,040,147 describes methods which use C-reactive protein, cytokines, and cellular adhesion molecules to characterize an individual's risk of developing a cardiovascular disorder. Although useful, these markers may be found in the blood of individuals with inflammation due to causes other than CVD, and thus, these markers may not be specific enough. Moreover, modulation of their levels has not been shown to predict a decrease in the morbidity or mortality of CVD.

The present invention provides methods for characterizing a subject's, particularly a human subject's, risk of having cardiovascular disease. The present invention also provides methods of characterizing a subject's risk of developing cardiovascular disease. In another embodiment, the present invention provides methods for characterizing a subject's risk of experiencing a complication of cardiovascular disease. In another embodiment, the present invention provides a method for determining whether a subject presenting with chest pain is at risk near term of experiencing a heart attack or other major adverse cardiac event. The present methods are especially useful for identifying those subjects who are in need of highly aggressive CVD therapies as well as those subjects who require no therapies targeted at inhibiting or preventing CVD or complications of CVD.

In one embodiment, the present methods comprise determining the levels of one or more oxidized biomolecules (referred to hereinafter collectively as oxidized "apolipoprotein A1-related biomolecules") in a bodily sample obtained from the subject. In one embodiment the oxidized apolipoprotein A1 ("apoA-I")-related biomolecule is oxidized high-density lipoprotein "HDL". In another embodiment, the oxidized apoA-I-related biomolecule is oxidized apoA-I. In another embodiment, the oxidized apoA-I-related biomolecule is an oxidized apoA-I peptide fragment. Levels of one or more of the oxidized apoA-I-related biomolecules in a biological sample from the subject may be compared to a control value that is derived from measurements of the one or more oxidized apoA-I-related biomolecules in comparable biological samples obtained from a population of control subjects. Levels of the one or more oxidized apoA-I-related biomolecules in a biological sample obtained from the subject, alternatively, may be compared to levels of an oxidized internal standard in the biological sample obtained from the subject. Examples of such internal standards include, but are not limited to, oxidized albumin or oxidized total protein.

In one embodiment, the comparison characterizes the subject's present risk of having CVD, as determined using standard protocols for diagnosing CVD. Moreover, the extent of the difference between the subject's oxidized apoA-I-related biomolecule levels and the control value is also useful for characterizing the extent of the risk and thereby, determining which subjects would most greatly benefit from certain therapies. In another embodiment, the comparison characterizes the subject's risk of developing CVD in the future. In another embodiment, the comparison can be used to characterize the subject's risk of experiencing a complication of CVD. The present methods can also be used to determine if a subject presenting with chest pain is at risk of experiencing a major adverse cardiac event, such as a myocardial infarction, reinfarction, the need for revascularization, or death, near term, e.g., within the following day, 3 months or 6 months after the subject presents with chest pain.

Also provided herein are methods for monitoring over time the status of CVD in a subject. In one embodiment, the method comprises determining the levels of one or more of the oxidized apoA-I-related biomolecules in a biological sample taken from the subject at an initial time and in a corresponding biological sample taken from the subject at a subsequent time. An increase in levels of the one or more oxidized apoA-I-related biomolecules in a biological sample taken at the subsequent time as compared to the initial time indicates that a subject's risk of having CVD has increased. A decrease in levels of the one or more oxidized apoA-I-related molecules indicates that the subject's risk of having CVD has decreased. For those subjects who have already experienced an acute adverse cardiovascular event such as a myocardial infarction or ischemic stroke, such methods are also useful for assessing the subject's risk of experiencing a subsequent acute adverse cardiovascular event. In such subjects, an increase in levels of the one more oxidized apoA-I-related biomolecules indicates that the subject is at increased risk of experiencing a subsequent adverse cardiovascular event. A decrease in levels of the one or more oxidized apoA-I-related biomolecules in the subject over time indicates that the subject's risk of experiencing a subsequent adverse cardiovascular event has decreased.

In another embodiment, the present invention provides a method for characterizing a subject's response to therapy directed at stabilizing or regressing CVD. The method comprises determining levels of one or more oxidized apoA-I-related biomolecules in a biological sample taken from the subject prior to therapy and determining the level of the one or more of the oxidized apo-A1 related biomolecules in a corresponding biological sample taken from the subject during or following therapy. A decrease in levels of the one or more oxidized apoA-I-related biomolecules in the sample taken after or during therapy as compared to levels of the one or more oxidized apo-A1-related biomolecules in the sample taken before therapy is indicative of a positive effect of the therapy on cardiovascular disease in the treated subject.

In another embodiment, the present invention provides antibodies that are immunospecific for one or more of the oxidized apoA-I related biomolecules used in the present methods. Such antibodies are useful for determining or measuring the levels of the apoA-I-related biomolecules in biological samples obtained from the subject.

In another embodiment, the present invention relates to kits that comprise reagents for assessing levels of oxidized HDL, oxidized apoA-I, and/or oxidized apoA-I peptide fragments in biological samples obtained from a test subject. The present kits also comprise printed materials such as instructions for practicing the present methods, or information useful for assessing a test subject's risk of CVD. Examples of such information include, but are not limited cut-off values, sensitivities at particular cut-off values, as well as other printed material for characterizing risk based upon the outcome of the assay. In some embodiments, such kits may also comprise control reagents, e.g. oxidized HDL, oxidized apoA-I, and/or oxidized apoA-I peptide fragments.

In another embodiment, the present invention relates to methods of treating a subject to reduce the risk of cardiovascular disease.

BRIEF DESCRIPTION OF THE FIGURES

FIG. 3. Summary of the apoA-I modification sites. The specific tyrosine residues that were modified by the respective reactions are indicated. The amino acid sequence (SEQ ID NO. 1) is based on NCBI accession number 229513 for the mature apoA-I protein. The numbering of all amino acid residues cited in this paper refers to this amino acid sequence of the mature protein.

FIG. 7. Detection of nitrated peptides in apoA-I isolated from human atheroma tissue by LC-tandem mass spectrometry. Selected reaction monitoring chromatograms (SRM) for the detection, in vivo, of un-modified, nitrated, and chlorinated peptides, after in-gel tryptic digestion of apoA-I immunoaffinity purified from human atheroma tissue. A) The detection of the un-modified and nitrated forms of peptide containing the favored Y192 site determined by the in vitro experiments. B) The CID spectrum recorded at this retention time to confirm the identity of the peptide and position of the nitration. C) The detection of the un-modified, nitrated, and chlorinated forms (top to bottom, respectively) of the peptide containing the secondary Y166 site. Again, the CID spectra recorded at this retention time (D) confirm the identity of the peptides and the position of the nitration and chlorination. The CID spectrum of the nitrated peptide is unambiguous while the CID spectrum of the molecular ion of the putative chlorinated peptide also shows significant overlap with the trihydroxyphenylalanine-containing form of this peptide that co-elutes and has a similar molecular weight.

DETAILED DESCRIPTION OF THE INVENTION

Figure 1:
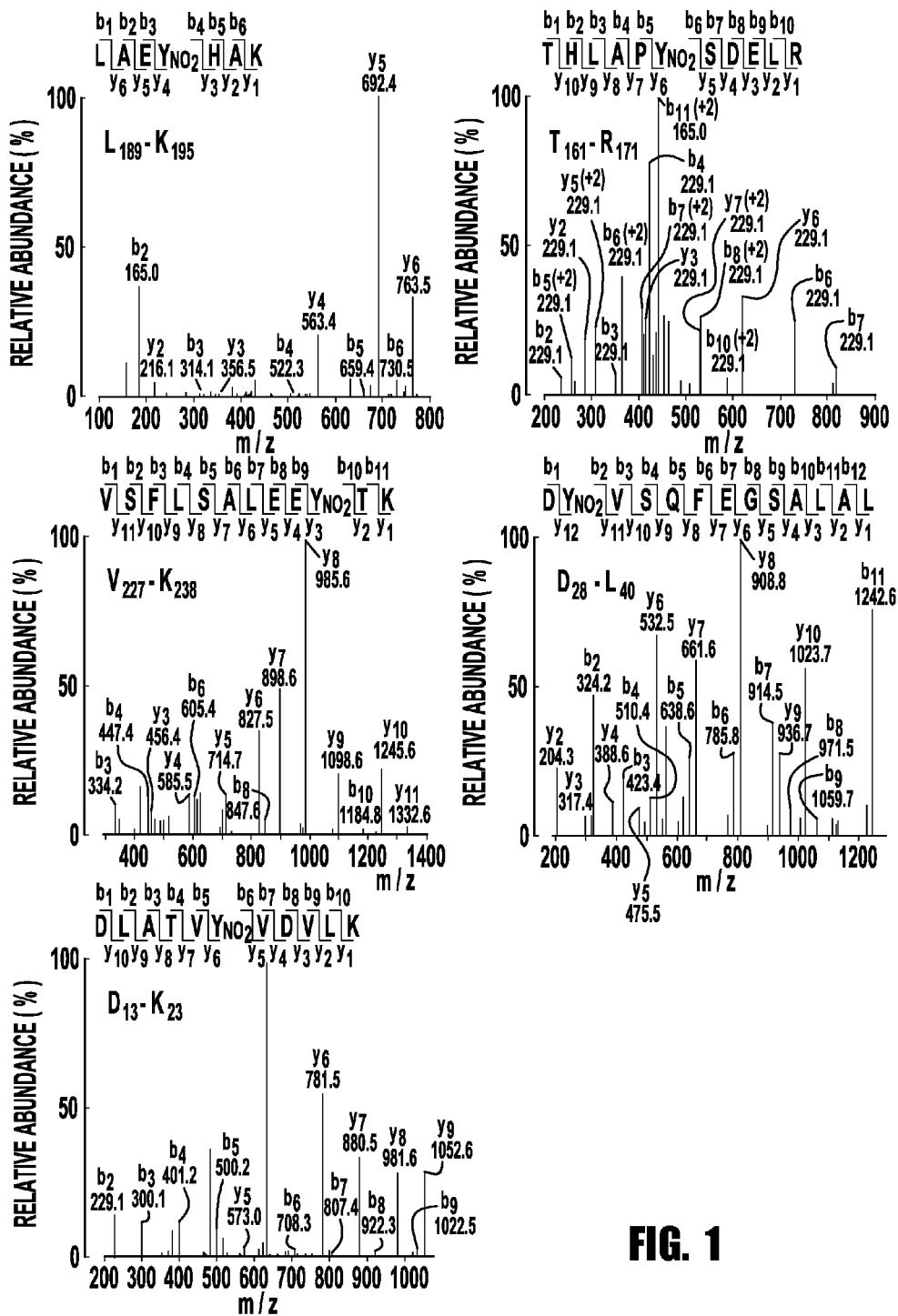
FIG. 1. Collision-induced dissociation (CID) spectra of the nitrotyrosine-containing peptides. The spectra were acquired during the analysis of in-gel tryptic digests of the apoA-I band from HDL treated with either the $MPO/H_2O_2/NO_2^-$ protein nitration system (A-D) or peroxynitrite (E), as described in the methods. Doubly and triply charged ions (as indicated) were detected and fragmented in an LC-tandem MS experiment using an ion trap mass spectrometer system. The peptides sequenced in spectra A and D were detected in the MPO-mediated reaction only. The peptides sequenced in spectra B and C were detected in both the MPO-mediated and peroxynitrite-mediated reactions. The peptide sequenced in spectrum E was detected only in the peroxynitrite-mediated reaction.

The present invention will now be described by reference to more detailed embodiments, with occasional reference to the accompanying drawings. This invention may, however, be embodied in different forms and should not be construed as limited to the embodiments set forth herein. Rather these embodiments are provided so that this disclosure will be thorough and complete, and will convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values; however, inherently contain certain errors necessarily resulting from error found in their respective measurements.

All publications, patent applications, patents, and other references mentioned herein are incorporated by reference in their entirety.

Methods and Markers for Predicting Risk of Cardiovascular Disease

Provided herein are methods and markers for characterizing a subject's risk for developing CVD, having CVD, or experiencing a complication of CVD. In this context, such methods and markers are useful for characterizing a subject's risk of having vulnerable plaque or experiencing a myocardial infarction.

In one embodiment, the method comprises determining levels of one or more oxidized apoA-I-related biomolecule in a biological sample obtained from the subject. In one embodiment, at least one of the oxidized apo-A1 related biomolecules is an oxidized form of HDL. The term "high density lipoprotein" or "HDL" as used herein is defined in accordance with common usage of those of skill in the art.

In another embodiment, at least one of the oxidized apoA-I-related biomolecules is an oxidized form of apolipoprotein A1. In another embodiment, at least one of the oxidized apoA-I related biomolecules is an oxidized apoA-I peptide fragment. Such fragment is three (3) or more amino acids in length and, except for the oxidized amino acid residues contained therein, comprises an amino acid sequence identical to a portion of SEQ ID NO. 1. In certain embodiments such apoA-I peptide fragments comprise one or more oxidized amino acids that indicate that the apoA-I protein from which the peptide has been derived was oxidized by a myeloperoxidase ("MPO")-related system. In certain embodiments, the oxidized amino acid is at any one of positions 18, 29, 166, 192, 236, or any combination thereof, in SEQ ID NO. 1. ApoA-I oxidation may take place by exposure to MPO-generated reactive chlorinating species (like those formed by the MPO/$H_2O_2$/$Cl^-$ system, or HOCl), or MPO-related reactive nitrogen species (like those formed by the MPO/$H_2O_2$/$NO_2^-$ system, or $ONOO^-$), or alternative MPO-related oxidation pathways (e.g. MPO-generated tyrosyl radical generating systems). Thus, examples of suitable peptides include, but are not limited to, apoA-I peptide fragments that comprise chlorotyrosine, nitrotyrosine, dityrosine, methionine sulfoxide, oxohistidine, trihydroxyphenylalanine, dihydroxyphenylalanine, tyrosine peroxide, or other oxidized amino acids formed by exposure of ApoA-I to MPO-generated oxidants. Examples of suitable apoA-I peptide fragments include, but are not limited to the peptides shown in Table I below.

| | $H_2O_2$ (µM) | | |
|---|---|---|---|
| | 10 | 25 | 100 |
| HDL + MPO/$H_2O_2$/$Cl^-$ Major modified peptidesdetected by ESI/MS/MS | | | |
| $L_{189}$AEY$_{Cl}$HAK$_{195}$ (SEQ ID NO 4) | ◆ | ◆ | ◆ |
| $T_{161}$HLAPY$_{Cl}$SDLR$_{170}$ (SEQ ID NO 5) | | ◆ | ◆ |
| $D_{28}$Y$_{Cl}$GSALGK$_{40}$ (SEQ ID NO 6) | | | ◆ |
| $V_{227}$SFLSALEEY$_{Cl}$TK$_{238}$ (SEQ ID NO 7) | | | ◆ |
| HDL + $ONOO^-$ Major modified peptides detected | | | |
| $T_{161}$HLAPY$_{NO2}$SDLR$_{170}$ (SEQ ID NO 5) | | | |
| $D_{13}$LATVY $_{NO2}$VDVLK$_{23}$ (SEQ ID NO 8) | | | |
| $V_{227}$SFLSALEEY$_{NO2}$TK$_{238}$ (SEQ ID NO. 7) | | | |

Levels of the one or more oxidized apoA-I-related biomolecules in the bodily sample of the test subject may then be compared to a control value that is derived from levels of the one or more apoA-I-related biomolecules in comparable bodily samples of control subjects. In an alternative embodiment, levels of the one or more oxidized apoA-I-related biomolecules in the bodily sample of the test subject may then be compared to an internal standard based on levels of other oxidized biomolecules in the subject's bodily sample. Examples of suitable internal standard moleculess include, but are not limited to levels of oxidized total protein in the subject's bodily sample and levels of oxidized albumin in the subject's bodily sample. Test subjects whose levels of the one or more apoA-I-related biomolecules are above the control value or in the higher range of control values are at greater risk of having or developing cardiovascular disease than test subjects whose levels of the one more apoA-I-related biomolecules are at or below the control value or in the lower range of control values. Moreover, the extent of the difference between the subject's oxidized apoA-I-related biomolecule levels and the control value is also useful for characterizing the extent of the risk and thereby, determining which subjects would most greatly benefit from certain therapies.

In certain embodiments, the subject's risk profile for CVD is determined by combining a first risk value, which is obtained by comparing levels of one or more apoA-I related biomolecules in a bodily sample of the subject with levels of said one or more apoA-I-related biomolecules in a control population, with one or more additional risk values to provide a final risk value. Such additional risk values may be obtained by procedures including, but not limited to, determining the subject's blood pressure, assessing the subject's response to a stress test, determining levels of myeloperoxidase, C-reactive protein, low density lipoprotein, or cholesterol in a bodily sample from the subject, or assessing the subject's atherosclerotic plaque burden.

In one embodiment, the method is used to assess the test subject's risk of having cardiovascular disease. Medical procedures for determining whether a human subject has coronary artery disease or is at risk for experiencing a complication of coronary artery disease include, but are not limited to, coronary angiography, coronary intravascular ultrasound (IVUS), stress testing (with and without imaging), assessment of carotid intimal medial thickening, carotid ultrasound studies with or without implementation of techniques of virtual histology, coronary artery electron beam computer tomography (EBTC), cardiac computerized tomography (CT) scan, CT angiography, cardiac magnetic resonance imaging (MRI), and magnetic resonance angiography (MRA.). Because cardiovascular disease, typically, is not limited to one region of a subject's vasculature, a subject who is diagnosed as having or being at risk of having coronary artery disease is also considered at risk of developing or having other forms of CVD such as cerebrovascular disease, aortic-iliac disease, and peripheral artery disease. Subjects who are at risk of having cardiovascular disease are at risk of having an abnormal stress test or abnormal cardiac catherization. Subjects who are at risk of having CVD are also at risk of exhibiting increased carotid intimal medial thickness and coronary calcification, characteristics that can be assessed using non-invasive imaging techniques. Subjects who are at risk of having CVD are also at risk of having an increased atheroscleorotic plaque burden, a characteristic that can be examined using intravascular ultrasound.

In another embodiment, the present methods are used to assess the test subject's risk of developing cardiovascular disease in the future. In one embodiment, the test subject is an apparently healthy individual. In another embodiment, the subject is not otherwise at elevated risk of having cardiovascular disease. In another embodiment, the present methods are used to determine if a subject presenting with chest pain is at risk of experiencing a heart attack or other major adverse cardiac event, such as a heart attack, a myocardial infarction, reinfarction, the need for revascularization, or death, near term. after the subject presents with chest pain. As used herein, the term "near term" means within one year. Thus, subjects who are at near term risk may be at risk of experiencing a major adverse cardiac event within the following day, 3 months, or 6 months after presenting with chest pain.

The present invention also provides a method for monitoring over time the status of CVD in a subject who has been diagnosed as having CVD. In this context, the method is also useful for monitoring the risk for athersclerotic progression or regression in a subject with CVD. In one embodiment, the method comprises determining the levels of one or more of the oxidized apoA-I-related biomolecules in a biological sample taken from the subject at an initial time and in a corresponding biological sample taken from the subject at a subsequent time. An increase in levels of the one or more oxidized apoA-I-related biomolecules in a biological sample taken at the subsequent time as compared to the initial time indicates that the subject's CVD has progressed or worsened. A decrease in levels of the one or more oxidized apoA-I-related molecules indicates that the CVD has improved or regressed. For those subjects who has already experienced an acute adverse cardiovascular event such as a myocardial infarction or ischemic stroke, such method can also be used to assess the subject's risk of having a subsequent acute adverse cardiovascular event. An increase over time in levels of the one or more oxidized apoA-I-related biomolecules in the subject indicates that a subject's risk of experiencing a subsequent adverse cardiovascular event has increased. A decrease over time in levels of the one or more oxidized apoA-I-related biomolecules in the subject indicates that that the subject's risk of experiencing a subsequent adverse cardiovascular event has decreased.

In another embodiment, the present invention provides a method for evaluating therapy in a subject suspected of having or diagnosed as having cardiovascular disease. The method comprises determining levels of one or more oxidized apoA-I-related biomolecules, including oxidized HDL, oxidized apoA-I, an oxidized peptide fragment of apoA-I, and combinations thereof, in a biological sample taken from the subject prior to therapy and determining levels of the one or more of the oxidized apo-A1 related biomolecules in a corresponding biological sample taken from the subject during or following therapy. A decrease in levels of the one or more oxidized apoA-I-related biomolecules in the sample taken after or during therapy as compared to levels of the one or more oxidized apo-A1-related biomolecules in the sample taken before therapy is indicative of a positive effect of the therapy on cardiovascular disease in the treated subject.

The present cardiovascular disease predictive methods are based, at least in part, on inventors' discovery that, as compared to total proteins, apoliprotein A1 in bodily samples obtained from subjects with cardiovascular disease is preferentially oxidized, e.g., nitrated or chlorinated. It is believed that the presence of these oxidized apoA-I related biomolecules are produced through MPO generated oxidants. MPO (donor: hydrogen peroxide, oxidoreductase, EC 1.11.1.7) is a tetrameric, heavily glycosylated, basic (PI. 10) heme protein of approximately 150 kDa. It is comprised of two identical disulfide-linked protomers, each of which possesses a protoporphyrin-containing 59-64 kDa heavy subunit and a 14 kDa light subunit (Nauseef, W. M, et al., *Blood* 67:1504-1507; 1986.)

MPO is abundant in neutrophils and monocytes, accounting for 5%, and 1 to 2%, respectively, of the dry weight of these cells (Nauseef, W. M, et al., *Blood* 67:1504-1507; 1986, (Hurst, J. K. In: Everse J.; Everse K.; Grisham M. B., eds. Peroxidases in chemistry and biology 1st ed. Boca Raton: CRC Press; 1991:37-62.) The heme protein is stored in primary azurophilic granules of leukocytes and secreted into both the extracellular milieu and the phagolysosomal compartment following phagocyte activation by a variety of agonists (Klebanoff, S. J, et al. *The neutrophil: functions and clinical disorders*. Amsterdam: Elsevier Scientific Publishing Co.; 1978.)

A recently proposed working kinetic model for MPO is shown in FIG. 12. MPO is a complex heme protein which possesses multiple intermediate states, each of which are influenced by the availability of reduced oxygen species such as $O_2^-$ and $H_2O_2$, and nitric oxide (NO, nitrogen monoxide) (Abu-Soud, H. M., et al., *J. Biol. Chem.* 275:5425-5430; 2000). At ground state, MPO exists in the ferric (Fe(III)) form. Upon addition of $H_2O_2$, the heme group of MPO is oxidized by two $e^-$ equivalents forming a reactive ferryl π cation radical intermediate termed Compound I. In the presence of halides such as $Cl^-$, $Br^-$, and $I^-$, and the psuedohalide thiocyanate ($SCN^-$), Compound I is readily reduced in a single two $e^-$ step, regenerating MPO-Fe(III) and the corresponding hypohalous acid (HOX). At plasma levels of halides and thiocyanate (100 mM $Cl^-$ 100 mM $Br^-$, 50 mM $SCN^-$, 100 nM $I^-$, chloride is a preferred substrate and hypochlorous acid (HOCl), a potent chlorinating oxidant, is formed (Foote, C. S., et al; *Nature* 301:715-726; 1983, Weiss, S. J., et al. *J. Clin. Invest.* 70:598-607; 1982).

Compound I can also oxidize numerous organic substrates while the heme undergoes two sequential one $e^-$ reduction steps, generating compound II and MPO-Fe(III), respectively (FIG. 12). Low molecular weight compounds primarily serve as substrates for MPO, generating diffusible oxidants and free radical species which can then convey the oxidizing potential of the heme to distant targets. In addition to halides and $SCN^-$, some of the naturally occurring substrates for MPO include nitrite ($NO_2$) (van der Vliet, A., et al., *J. Biol. Chem.* 272: 7617-7625; 1997), tyrosine (van der Vliet, A., et al., *J. Biol. Chem.* 272:7617-7625; 1997), ascorbate (Marquez, L. A., et al., *J. Biol. Chem.* 265:5666-5670; 1990), urate (Maehly, H. C. *Methods Enzymol.* 2:798-801; 1955), catecholamines (Metodiewa, D., et al., *Eur. J. Biochem.* 193:445-448; 1990), estrogens (Klebanoff, S. J. *J. Exp. Med.* 145:983-998; 1977), and serotonin (Svensson, B. E. *Chem. Biol. Interact.* 70:305-321; 1989). MPO-Fe(III) can also be reduced to an inactive ferrous form, MPO-Fe(II) (Hurst, J. K. In: Everse J.; Everse K.; Grisham M. B., eds. Peroxidases in chemistry and biology 1st ed. Boca Raton: CRC Press; 1991:37-62, (Kettle, A. J., et al., *Redox. Rep.* 3:3-15; 1997). MPO-Fe(II) and MPO-Fe(II) bind to $O_2^-$, and $O_2$, respectively, forming a ferrous dioxy intermediate, compound III (MPO-Fe(II)-$O_2$) (FIG. 12). Spectral studies demonstrate that addition of $H_2O_2$ to Compound III ultimately forms compound II. Thus, compound III may indirectly promote one $e^-$ peroxidation reactions.

Recent studies identify a role for NO, a relatively long-lived free radical generated by nitric oxide synthase (NOS), in modulating MPO peroxidase activity (Abu-Soud, H. M., et al., *J. Biol. Chem.* 275:5425-5430; 2000). MPO and the inducible isoform of NOS are colocalized in the primary granule of leukocytes. During phagocyte activation, such as during ingestion of bacteria, MPO and NOS are secreted into the phagolysosome and extracellular compartments, and nitration of bacterial proteins is observed (Evans, T. J., et al., *Proc. Natl. Acad. Sci. USA* 93:9553-9558; 1996). Rapid kinetics studies demonstrate that at low levels of NO, the initial rate of MPO-catalyzed peroxidation of substrates is enhanced. The mechanism is through acceleration of the rate-limiting step in MPO catalysis, reduction of compound II to MPO-Fe(III) (FIG. 1) (Abu-Soud, H. M., et al., *J. Biol. Chem.* 275:5425-5430; 2000, Abu-Soud, H. M., et al. Nitric oxide is a physiological substrate for mammalian animal peroxidases. *J. Biol. Chem.* 275:37524-37532, 2000). At higher levels of NO, reversible inhibition of MPO occurs through formation of a spectroscopically distinguishable nitrosyl complex, MPO-Fe(III)-NO (Abu-Soud, H. M., et al., *J. Biol. Chem.* 275:5425-5430; 2000). NO also can serve as a substrate for MPO compound I, resulting in its reduction to Compound II (Id.). Furthermore, in the presence of NO, the overall turnover rate of MPO through the peroxidase cycle is enhanced nearly 1000-fold (Id.). Finally, NO also reversibly binds to MPO-Fe (II) forming the corresponding MPO-Fe(II)-NO intermediate, which is in equilibrium with MPO-Fe(II) and MPO-Fe (III)-NO (FIG. 1) (Abu-Soud, H. M., et al., *J. Biol. Chem.* 275:5425-5430; 2000, Abu-Soud, H. M., et al. Nitric oxide is a physiological substrate for mammalian animal peroxidases. *J. Biol. Chem.* 275:37524-37532, 2000).

As described above, MPO can utilize a variety of cosubstrates with $H_2O_2$ to generate reactive oxidants as intermediates. Many stable end-products generated by these species have been characterized and shown to be enriched in proteins, lipids, and LDL recovered from human atherosclerotic lesions (Chisolm, G. M., et al., *Proc. Natl. Acad. Sci. USA* 91:11452-11456; 1994, Hazell, L. J., et al., *J. Clin. Invest.* 97:1535-1544; 1996, Hazen, S. L., et al., *J. Clin. Invest.* 99:2075-2081; 1997, Leeuwenburgh, C., et al, *J. Biol. Chem.* 272:1433-1436; 1997, Leeuwenburgh, C., et al., *J. Biol. Chem.* 272:3520-3526; 1997). FIG. 13 summarizes some of the reactive intermediates and products formed by MPO, any of which are known to be enriched in vascular lesions.

Biological Samples

Suitable biological samples useful for predicting or monitoring cardiovascular disease in a subject or for assessing the effect of therapeutic agents on subjects with cardiovascular disease include but are not limited to whole blood samples, samples of blood fractions, including but not limited to serum and plasma. The sample may be fresh blood or stored blood (e.g. in a blood bank) or blood fractions. The sample may be a blood sample expressly obtained for the assays of this invention or a blood sample obtained for another purpose which can be subsampled for the assays of this invention.

In one embodiment, the biological sample is whole blood. Whole blood may be obtained from the subject using standard clinical procedures. In another embodiment, the biological sample is plasma. Plasma may be obtained from whole blood samples by centrifugation of anti-coagulated blood. Such process provides a buffy coat of white cell components and a supernatant of the plasma. In another embodiment, the biological sample is serum. Serum may be obtained by centrifugation of whole blood samples that have been collected in tubes that are free of anti-coagulant. The blood is permitted to clot prior to centrifugation. The yellowish-reddish fluid that is obtained by centrifugation is the serum.

The sample may be pretreated as necessary by dilution in an appropriate buffer solution, heparinized, concentrated if desired, or fractionated by any number of methods including but not limited to ultracentrifugation, fractionation by fast performance liquid chromatography (FPLC), or precipitation of apolipoprotein B containing proteins with dextran sulfate or other methods. Any of a number of standard aqueous buffer solutions, employing one of a variety of buffers, such as phosphate, Tris, or the like, at physiological pH can be used.

Subjects

The subject is any human or other animal to be tested for characterizing its risk of CVD. In certain embodiments, the subject does not otherwise have an elevated risk of an adverse cardiovascular event. Subjects having an elevated risk of an adverse cardiovascular event include those with a family history of cardiovascular disease, elevated lipids, smokers, prior acute cardiovascular event, etc. (See, e.g., Harrison's Principles of Experimental Medicine, 15th Edition, McGraw-Hill, Inc., N.Y.—hereinafter "Harrison's").

In certain embodiments the subject is an apparently healthy nonsmoker. "Apparently healthy", as used herein, means individuals who have not previously being diagnosed as having any signs or symptoms indicating the presence of atherosclerosis, such as angina pectoris, history of an acute adverse cardiovascular event such as a myocardial infarction or stroke, evidence of atherosclerosis by diagnostic imaging methods including, but not limited to coronary angiography. Apparently healthy individuals also do not otherwise exhibit symptoms of disease. In other words, such individuals, if examined by a medical professional, would be characterized as healthy and free of symptoms of disease. "Nonsmoker" means an individual who, at the time of the evaluation, is not a smoker. This includes individuals who have never smoked as well as individuals who in the past have smoked but presently no longer smoke.

Immunoassays for Determining Levels of Oxidized HDL, apoA-I and apoA-I Peptide Fragments Levels of the oxidized HDL, apoA-I, and apoA-I peptide fragments in the biological sample can be determined using polyclonal or monoclonal antibodies that are immunoreactive with such oxidized biomolecule. For example, antibodies immunospecific for nitrotyrosine containing apoA-I peptide fragments may be made and labeled using standard procedures and then employed in immunoassays to detect the presence of such nitrotyrosine containing apoA-I peptide in the sample. Suitable immunoassays include, by way of example, radioimmunoassays, both solid and liquid phase, fluorescence-linked assays, competitive immunoassays, or enzyme-linked immunosorbent assays. In certain embodiments, the immunoassays are also used to quantify the amount of the oxidized biomolecule that is present in the sample.

Monoclonal antibodies raised against the select oxidized polypeptide species are produced according to established procedures. Generally, the oxidized apoA-I protein or apoA-I peptide fragment is used to immunize a host animal.

Suitable host animals, include, but are not limited to, rabbits, mice, rats, goats, and guinea pigs. Various adjuvants may be used to increase the immunological response in the host animal. The adjuvant used depends, at least in part, on the host species. Such animals produce heterogenous populations of antibody molecules, which are referred to as polyclonal antibodies and which may be derived from the sera of the immunized animals.

Monoclonal antibodies, which are homogenous populations of an antibody that bind to a particular antigen, are obtained from continuous cells lines. Conventional techniques for producing monoclonal antibodies are the hybridoma technique of Kohler and Millstein (Nature 356:495-497 (1.975)) and the human B-cell hybridoma technique of Kosbor et al (Immunology Today 4:72 (1983)). Such antibodies may be of any immunoglobulin class including IgG, IgM, IgE, Iga, IgD and any class thereof. Procedures for preparing antibodies against modified amino acids, such as for example, 3-nitrotyrosine are described in Ye, Y. Z., M. Strong, Z. Q. Huang, and J. S. Beckman. 1996. Antibodies that recognize nitrotyrosine. *Methods Enzymol.* 269:201-209.

Preparation of Antibodies

The oxidized apoA-I protein or oxidized apoA-I peptide fragment can be used as an immunogen to produce antibodies immunospecific for the oxidized protein or peptide fragment. The term "immunospecific" means the antibodies have substantially greater affinity for the oxidized apoA-I protein or apoA-I peptide fragment than for other proteins or polypeptides, including the un-oxidized apoA-I protein or apoA-I peptide fragment. Such antibodies may include, but are not limited to, polyclonal, monoclonal, chimeric, single chain, and Fab fragments.

The oxidized apoA-I peptide fragments are at least three amino acids in length and comprise a modified apoA-I protein sequence, i.e., the peptide comprises a sequence that, except for the presence of an oxidized amino acid, particularly an oxidized tyrosine residue, is identical to a sequence in SEQ ID NO. 1. The apoA-I peptide fragments can be 3 amino acids in length. In other embodiments, the apoA-I peptide fragment is 4, 5, 6, 7, 8, 9, or 10 amino acids in length. In other embodiments, the apoA-I peptide fragment is 11-20, 21-30, 31-40, 41-50, 51-60, 61-70, 71-80, 81-90, 91-100, 101-110, 111-120, 121-130, 131-140, 141-150, 151-160, 161-170, 171-180, 181-190, 191-200, 201-210, 211-220, 221-230, or 231-242 amino acids in length.

Peptides that are less than 6 amino acids in length conventionally are fused with those of another protein such as keyhole limpet hemocyanin and antibody chimeric molecule. Larger fragments, e.g., apoA-I peptide fragments that are from 6 to 242 amino acids in length may also be used as the immunogen. The structure of larger immunogenic fragments of the apoA-I protein can be determined using software programs, for example the MacVector program, to determine hydrophilicity and hydrophobicity and ascertain regions of the protein that are likely to be present at the surface of the molecule.

Polyclonal antibodies are generated using conventional techniques by administering the apoA-I protein or apoA-I peptide fragment. or apoA-I to a host animal. Depending on the host species, various adjuvants may be used to increase immunological response. Among adjuvants used in humans, Bacilli-Calmette-Guerin (BCG), and *Corynebacterium parvum*. are especially preferable. Conventional protocols are also used to collect blood from the immunized animals and to isolate the serum and or the IgG fraction from the blood.

For preparation of monoclonal antibodies, conventional hybridoma techniques are used. Such antibodies are produced by continuous cell lines in culture. Suitable techniques for preparing monoclonal antibodies include, but are not limited to, the hybridoma technique, the human B-cell hybridoma technique, and the EBV hybridoma technique.

Various immunoassays may be used for screening to identify antibodies having the desired specificity. These include protocols that involve competitive binding or immunoradiometric assays and typically involve the measurement of complex formation between the respective oxidized apoA-I polypeptide and the antibody.

The present antibodies may be used to detect the presence of or measure the amount of oxidized HDL, oxidized apoA-I, and oxidized apoA-I peptide fragments in a biological sample from the subject. The method comprises contacting a sample taken from the individual with one or more of the present antibodies; and assaying for the formation of a complex between the antibody and a protein or peptide in the sample. For ease of detection, the antibody can be attached to a substrate such as a column, plastic dish, matrix, or membrane, preferably nitrocellulose. The sample may be a tissue or a biological fluid, including urine, whole blood, or exudate, preferably serum. The sample may be untreated, subjected to precipitation, fractionation, separation, or purification before combining with the antibody. Interactions between antibodies in the sample and the isolated HDL, protein or peptide are detected by radiometric, colorimetric, or fluorometric means, size-separation, or precipitation. Preferably, detection of the antibody-protein or peptide complex is by addition of a secondary antibody that is coupled to a detectable tag, such as for example, an enzyme, fluorophore, or chromophore. Formation of the complex is indicative of the presence of oxidized HDL, apoA-I or apoA-I peptide fragments in the individual's biological sample.

In certain embodiments, the method employs an enzyme-linked immunosorbent assay (ELISA) or a Western immunoblot procedure.

Additional Methods for Measuring of Oxidized HDL, Oxidized apoA-I And Oxidized apoA-I Peptide Fragments Mass spectrometry-based methods (e.g. LC/ESI/MS/MS) may also be used to assess levels of oxidized HDL, oxidized apoA-I and oxidized apoA-I peptide fragments in the biological sample as shown in the examples below. Such methods are standard in the art and include, for example, HPLC with on-line electrospray ionization tandem mass spectometry. Synthetic standard tryptic digets peptides for parent (unmodified) and modified (nitrated, chlorinated) forms can be made readily with automated peptide synthesizers using commercially available fmoc modified amino acids. The parent molecules i.e., the unmodified HDL, apoA-I, and apoA-I peptide fragments will have different masses than the oxidized molecules because of added moieties, added $NO_2$ or $Cl^-$ moiety, for example). Thus, distinct parent→daughter ion transitions for each peptide would be achievable. Adding the nitro group to Tyr changes the pKa of the phenoxy hydrogen on the Tyr from 10 to 7. Thus, charge differences and changes in polarity between modified and non-modified peptide have high likelihood of showing distinct retention times on HPLC as well.

Control Value

Levels of the oxidized HDL, apoA-I and/or apoA-I polypeptide in the biological sample obtained from the test subject may compared to a control value. The control value is based upon levels of oxidized HDL, apoA-I, and/or apoA-I, respectively, in comparable samples obtained from a control population, e.g., the general population or a select population of human subjects. For example, the select population may be comprised of apparently healthy subjects. "Apparently healthy", as used herein, means individuals who have not previously had any signs or symptoms indicating the presence of atherosclerosis, such as angina pectoris, history of an acute adverse cardiovascular event such as a myocardial infarction or stroke, evidence of atherosclerosis by diagnostic imaging methods including, but not limited to coronary angiography. Apparently healthy individuals also do not otherwise exhibit symptoms of disease. In other words, such individuals, if examined by a medical professional, would be characterized as healthy and free of symptoms of disease. In another example, the control value can be derived from an apparently healthy nonsmoker population. "Nonsmoker", as used herein, means an individual who, at the time of the evaluation, is not a smoker. This includes individuals who have never smoked as well as individuals who in the past have smoked but presently no longer smoke. An apparently healthy, non-smoker population may have a different normal range of oxidized HDL, apoA-I and/or apoA-I peptide fragment than will a smoking population or a population whose member have had a prior cardiovacular disorder. Accordingly, the control values selected may take into account the category into which the test subject falls. Appropriate categories can be selected with no more than routine experimentation by those of ordinary skill in the art.

The control value is related to the value used to characterize the level of the oxidized polypeptide obtained from the test subject. Thus, if the level of the oxidized polypeptide is an absolute value such as the units of oxidized apoA-I per ml of blood, the control-value is also based upon the units of oxidized apoA-I per ml of blood in individuals in the general population or a select population of human subjects. Similarly, if the level of the oxidized HDL, apoA-I, or apoA-I peptide fragment is a representative value such as an arbitrary unit obtained from a cytogram, the control value is also based on the representative value.

The control value can take a variety of forms. The control value can be a single cut-off value, such as a median or mean. The control value can be established based upon comparative groups such as where the risk in one defined group is double the risk in another defined group. The control values can be divided equally (or unequally) into groups, such as a low risk group, a medium risk group and a high-risk group, or into quadrants, the lowest quadrant being individuals with the lowest risk the highest quadrant being individuals with the highest risk, and the test subject's risk of having CVD can be based upon which group his or her test value falls.

Control values of oxidized HDL, apoA-I and/or apoA-I peptide fragment in biological samples obtained, such as for example, mean levels, median levels, or "cut-off" levels, are established by assaying a large sample of individuals in the general population or the select population and using a statistical model such as the predictive value method for selecting a positivity criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is specifically incorporated herein by reference. A "cutoff" value can be determined for each risk predictor that is assayed. The standardized method that was used in Example 1 below employs the guaiacol oxidation assay as described in Klebanoff, S. J., Waltersdorph, A. N. and Rosen, H. 1984. "Antimicrobial activity of myeloperoxidase". Methods in Enzymology. 105: 399-403).

Comparison of Oxidized Biomolecule from the Test Subject to the Control Value

Levels of each select oxidized biomolecule, i.e., oxidized HDL, oxidized apoA-I, oxidized apoA-I polypeptide fragment in the individual's biological sample may be compared to a single control value or to a range of control values. If the level of the present risk predictor in the test subject's biological sample is greater than the control value or exceeds or is in the upper range of control values, the test subject is at greater risk of developing or having CVD than individuals with levels comparable to or below the control value or in the lower range of control values. In contrast, if levels of the present risk predictor in the test subject's biological sample is below the control value or is in the lower range of control values, the test subject is at a lower risk of developing or having CVD than individuals whose levels are comparable to or above the control value or exceeding or in the upper range of control values. The extent of the difference between the test subject's risk predictor levels and control value is also useful for characterizing the extent of the risk and thereby, determining which individuals would most greatly benefit from certain aggressive therapies. In those cases, where the control value ranges are divided into a plurality of groups, such as the control value ranges for individuals at high risk, average risk, and low risk, the comparison involves determining into which group the test subject's level of the relevant risk predictor falls.

Alternatively, the level of oxidized biomolecule, i.e., oxidized HDL, oxidized apoA-I, or oxidized apoA-I peptide fragment may be compared to the level of an oxidized internal standard in the sample. Examples of suitable internal standards include, but are not limited to, levels of oxidized total protein in the sample or levels of oxidized albumin in the sample.

The present predictive tests are useful for determining if and when therapeutic agents that are targeted at preventing CVD or for slowing the progression of CVD should and should not be prescribed for a individual. For example, individuals with values of oxidized apoA-I above a certain cutoff value, or that are in the higher tertile or quartile of a "normal range," could be identified as those in need of more aggressive intervention with lipid lowering agents, life style changes, etc.

Evaluation of CVD Therapeutic Agents

Also provided are methods for evaluating the effect of CVD therapeutic agents on individuals who have been diagnosed as having or as being at risk of developing CVD. Such therapeutic agents include, but are not limited to, anti-inflammatory agents, insulin sensitizing agents, antihypertensive agents, anti-thrombotic agents, anti-platelet agents, fibrinolytic agents, lipid reducing agents, direct thrombin inhibitors, ACAT inhibitor, CDTP inhibitor thioglytizone, glycoprotein II b/IIIa receptor inhibitors, agents directed at raising or altering HDL metabolism such as apoA-I milano or CETP inhibitors (e.g., torcetrapib), or agents designed to act as artificial HDL. Such evaluation comprises determining the levels of one or more oxidized apoA-I-related biomolecules in a biological sample taken from the subject prior to administration of the therapeutic agent and a corresponding biological fluid taken from the subject following administration of the therapeutic agent. A decrease in the level of the selected risk markers in the sample taken after administration of the therapeutic as compared to the level of the selected risk markers in the sample taken before administration of the therapeutic agent is indicative of a positive effect of the therapeutic agent on cardiovascular disease in the treated subject.

Kits

Also provided are kits for practicing the present methods. Such kits contain reagents for assessing levels of oxidized apoA-I, oxidized apoA-I peptide fragments, oxidized HDL, or combinations thereof in a biological sample. In one embodiment, the reagent is an antibody that is immunospecfic for oxidized apoA-I, or an oxidized apoA-I peptide fragment, or both. In one embodiment, the kit also comprises instructions for using the reagent in the present methods. In another embodiment, the kit comprises information useful for determining a subject's risk of cardiovascular disease or a complication. Examples of such information include, but are not limited cut-off values, sensitivities at particular cut-off values, as well as other printed material for characterizing risk based upon the outcome of the assay. In some embodiments, such kits may also comprise control reagents, e.g. oxidized HDL, oxidized apoA-I, and/or oxidized apoA-I peptide fragments.

Therapeutic Methods

The present invention also relates to methods of treating a subject to reduce the risk of a cardiovascular disorder or complication of such disorder. In one embodiment, the method comprises determining levels of one or more apoA-I related biomolecules in a bodily sample of the subject, and where the levels of the one or more apoA-I related biomolecules are elevated as compared to levels in comparable bodily samples from a control population of subjects, administering to the subject an agent chosen from an anti-inflammatory agent, an antithrombotic agent, an anti-platelet agent, a fibrinolytic agent, a lipid reducing agent, a direct thrombin inhibitor, a glycoprotein IIb/IIIa receptor inhibitor, an agent that binds to cellular adhesion molecules and inhibits the ability of white blood cells to attach to such molecules, a calcium channel blocker, a beta-adrenergic receptor blocker, a cyclooxygenase-2 inhibitor, an angiotensin system inhibitor, and/or combinations thereof. The agent is administered in an amount effective to lower the risk of the subject developing a future cardiovascular disorder.

"Anti-inflammatory" agents include but are not limited to, Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium.

"Anti-thrombotic" and/or "fibrinolytic" agents include but are not limited to, Plasminogen (to plasmin via interactions of prekallikrein, kininogens, Factors XII, XIIIa, plasminogen proactivator, and tissue plasminogen activator[TPA]) Streptokinase; Urokinase: Anisoylated Plasminogen-Streptokinase Activator Complex; Pro-Urokinase; (Pro-UK); rTPA (alteplase or activase; r denotes recombinant); rPro-UK; Abbokinase; Eminase; Sreptase Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; retaplase; Trifenagrel; Warfarin; Dextrans.

"Anti-platelet" agents include but are not limited to, Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine; Anagrelide.

"Lipid-reducing" agents include but are not limited to, gemfibrozil, cholystyramine, colestipol, nicotinic acid, probucol lovastatin, fluvastatin, simvastatin, atorvastatin, pravastatin, cerivastatin, and other HMG-CoA reductase inhibitors.

"Direct thrombin inhibitors" include but are not limited to, hirudin, hirugen, hirulog, agatroban, PPACK, thrombin aptamers.

"Glycoprotein IIb/IIIa receptor inhibitors" are both antibodies and non-antibodies, and include but are not limited to ReoPro (abcixamab), lamifiban, tirofiban.

"Calcium channel blockers" are a chemically diverse class of compounds having important therapeutic value in the control of a variety of diseases including several cardiovascular disorders, such as hypertension, angina, and cardiac arrhythmias (Fleckenstein, Cir. Res. v. 52, (suppl. 1), p. 13-16 (1983); Fleckenstein, Experimental Facts and Therapeutic Prospects, John Wiley, New York (1983); McCall, D., Curr Pract Cardiol, v. 10, p. 1-11 (1985)). Calcium channel blockers are a heterogenous group of drugs that prevent or slow the entry of calcium into cells by regulating cellular calcium channels. (Remington, The Science and Practice of Pharmacy, Nineteenth Edition, Mack Publishing Company, Eaton, Pa., p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, aminone, amlodipine, bencyclane, felodipine, fendiline, flunarizine, isradipine, nicardipine, nimodipine, perhexylene, gallopamil, tiapamil and tiapamil analogues (such as 1993RO-11-2933), phenyloin, barbiturates, and the peptides dynorphin, omega-conotoxin, and omega-agatoxin, and the like and/or pharmaceutically acceptable salts thereof.

"Beta-adrenergic receptor blocking agents" are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hyd-roxypropoxy)-3-pyridenecarbonitrilHCl, 1-butylamino-3-(2,5-dichlorophenoxy-)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl- 2-thienyl)thiazol, 7-(2-hydroxy-3-t-butylaminpropoxy)phthalide. The above-identified compounds can be used as isomeric mixtures, or in their respective levorotating or dextrorotating form.

Suitable COX-2 inhibitors include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 N-benzyl indol-3-yl butanoic acid derivatives as cyclooxygenase inhibitors"; U.S. Pat. No. 5,677,318 Diphenyl-1, 2-3-thiadiazoles as anti-inflammatory agents"; U.S. Pat. No. 5,691,374 "Diaryl-5-oxygenated-2-(5H)-furanones as COX-2 inhibitors"; U.S. Pat. No. 5,698,584 "3,4-diaryl-2-hydroxy-2,5-d-ihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif.). Additional COX-2 inhibitors are also described in U.S. Pat. No. 5,643,933, assigned to G. D. Searle & Co. (Skokie, Ill.), entitled: "Substituted sulfonylphenylheterocycles as cyclooxygenase-2 and 5-lipoxygenase inhibitors."

An "angiotensin system inhibitor" is an agent that interferes with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin 1 from which angiotensin II is ultimately derived. The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin (renin-angiotensin) system inhibitors are compounds that act to interfere with the production of angiotensin II from angiotensinogen or angiotensin I or interfere with the activity of angiotensin II. Such inhibitors are well known to those of ordinary skill in the art and include compounds that act to inhibit the enzymes involved in the ultimate production of angiotensin II, including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists.

Examples of angiotensin II antagonists include: peptidic compounds (e.g., saralasin, [(San$^1$)(Val$^5$)(Ala$^8$)]angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., J. Pharmacol. Exp. Ther. 247(1), 1-7 (1988)); 4, 5,6,7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alanyl-(4, thiazolyl)-L-alanyl (35, 45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl)methyl]1H-imidazole-5-yl[methylane]-2-thiophenepropanoic acid, Smith Kline Beecham Pharmaceuticals, Pa.); Losartan (DUP7531MK954, DuPont Merck Pharmaceutical Company); Remikirin (CRO42-5892, F. Hoffman LaRoche AG); A.sub.2 agonists (Marion Merrill Dow) and certain non-peptide heterocycles (G. D. Searle and Company). Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

Examples of renin inhibitors that are the subject of United States patents are as follows: urea derivatives of peptides (U.S. Pat. No. 5,116,835); amino acids connected by nonpeptide bonds (U.S. Pat. No. 5,114,937); di and tri peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamrates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

In certain embodiments, the test subjects are apparently healthy subjects otherwise free of current need for treatment with the agent prescribed according to the present invention. For example, if treatment with a particular agent occurs based on elevated levels of oxidized apoA-I related biomolecules, then the patient is free of symptoms calling for treatment with that agent (or the category of agent into which the agent falls), other than the symptom of having elevated levels of apoA-I related biomolecules. In some embodiments, the subject is otherwise free of symptoms calling for treatment with any one of any combination of or all of the foregoing categories of agents. For example, with respect to anti-inflammatory agents, the subject is free of symptoms of rheumatoid arthritis, chronic back pain, autoimmune diseases, vascular diseases, viral diseases, malignancies, and the like. In another embodiment, the subject is not at an elevated risk of an adverse cardiovascular event (e.g., subject with no family history of such events, subjects who are nonsmokers, subjects who are nonhyperlipidemic, subjects who do not have elevated levels of a systemic inflammatory marker), other than having an elevated level of one or more oxidized apoA-I arelated biomolecules.

In some embodiments, the subject is a nonhyperlipidemic subject. A "nonhyperlipidemic" is a subject that is a nonhypercholesterolemic and/or a nonhypertriglyceridemic subject. A "nonhypercholesterolemic" subject is one that does not fit the current criteria established for a hypercholesterolemic subject. A nonhypertriglyceridemic subject is one that does not fit the current criteria established for a hypertriglyceridemic subject (See, e.g., Harrison's Principles of Experimental Medicine, 15th Edition, McGraw-Hill, Inc., N.Y.— hereinafter "Harrison's"). Hypercholesterolemic subjects and hypertriglyceridemic subjects are associated with increased incidence of premature coronary heart disease. A hypercholesterolemic subject has an LDL level of >160 mg/dL, or >130 mg/dL and at least two risk factors selected from the group consisting of male gender, family history of premature coronary heart disease, cigarette smoking (more than 10 per day), hypertension, low HDL (<35 mg/dL), diabetes mellitus, hyperinsulinemia, abdominal obesity, high lipoprotein (a), and personal history of cerebrovascular disease or occlusive peripheral vascular disease. A hypertriglyceridemic subject has a triglyceride (TG) level of >250 mg/dL. Thus, a nonhyperlipidemic subject is defined as one whose cholesterol and triglyceride levels are below the limits set as described above for both the hypercholesterolemic and hypertriglyceridemic subjects.

EXAMPLES

A. Protein Studies

Materials

L-[$^{13}C_6$]tyrosine and L-[$^{13}C_9$, $^{15}N_1$]tyrosine were purchased from Cambridge Isotopes Inc. (Andover, Mass.). Tissue culture media and additives were purchased from Life Technologies (Gaitherburg, Md.). RAW264.7 cells were obtained from the American Type Culture Collection (Rockville, Md.). [$^3$H]Cholesterol was obtained from Amersham (Piscataway, N.J.), and resuspended in ethanol prior to use. All other reagents were obtained from Sigma Chemical Co. (St. Louis, Mo.) unless otherwise specified.

Methods

General Procedures.

Peroxynitrite was synthesized and quantified as described (Beckman, J. S., Chen, J., Ischiropoulos, H., and Crow, J. P. 1994. Oxidative chemistry of peroxynitrite. *Methods in Enzymology* 233:229-240). L-3-[$^{13}C_6$]nitrotyrosine was synthesized from L-[$^{13}C_6$]tyrosine and peroxynitrite, and isolated by reverse phase HPLC to remove residual NO$_2^-$ prior to use (Wu, W., Chen, Y., and Hazen, S. L. 1999. Eosinophil peroxidase nitrates protein tyrosyl residues. Implications for oxidative damage by nitrating intermediates in eosinophilic inflammatory disorders. *Journal of Biological Chemistry.* 274: 25933-25944). Protein content was determined by the Markwell-modified Lowry protein assay (Markwell, M. A., Haas, S. M., Bieber, L. L., and Tolbert, N. E. 1978. A modification of the Lowry procedure to simplify protein determination in membrane and lipoprotein samples. *Analytical Biochemistry.* 87:206-210) with bovine serum albumin as standard. The concentration of reagent H$_2$O$_2$ was determined spectrophotometrically ($\epsilon_{240}$=39.4 M$^{-1}$cm$^{-1}$; ref. (Nelson, D. P., and Kiesow, L. A. 1972. Enthalpy of decomposition of hydrogen peroxide by catalase at 25 degrees C. (with molar extinction coefficients of H$_2$O$_2$ solutions in the UV). *Analytical Biochemistry.* 49:474-478). Myeloperoxidase (donor: hydrogen peroxide, oxidoreductase, EC 1.11.1.7) was initially purified from detergent extracts of human leukocytes by sequential lectin affinity and gel filtration chromatography as described by Rakita (Rakita, R. M., Michel, B. R., and Rosen, H. 1990. Differential inactivation of *Escherichia coli* membrane dehydrogenases by a myeloperoxidase-mediated antimicrobial system. *Biochemistry.* 29:1075-1080), and then trace levels of contaminating eosinophil peroxidase were then removed by passage over a sulphopropyl Sephadex column (Wever, R., Plat, H., and Hamers, M. N. 1981. Human eosinophil peroxidase: a novel isolation procedure, spectral properties and chlorinating activity. *FEBS Letters.* 123:327-331). Purity of isolated MPO was established by demonstrating a RZ of >0.84 (A$_{430}$/A$_{280}$), SDS PAGE analysis with Coomassie Blue staining, and in-gel tetramethylbenzidine peroxidase staining (van Dalen, C. J., Whitehouse, M. W., Winterbourn, C. C., and Kettle, A. J. 1997. Thiocyanate and chloride as competing substrates for myeloperoxidase. *Biochemical Journal.* 327:487-492). Enzyme concentration was determined spectrophotometrically utilizing an extinction coefficient of 89,000 M$^{-1}$cm$^{-1}$/heme of MPO (Agner, K. 1972. *Structure and function of oxidation-reduction enzymes.* Tarrytown, N.Y.: Pergamon Press. 329-335). Delipidated and purified apoA-I was purchased from Biodesign International (Saco, Me.) and used without further purification following demonstration of purity by SDS-PAGE and silver stain analysis, and lack of significant free fatty acids by HPLC with on-line tandem mass spectrometry analysis (Zhang, R., Brennan, M. L., Shen, Z., MacPherson, J. C., Schmitt, D., Molenda, C. E., and Hazen, S. L. 2002. Myeloperoxidase functions as a major enzymatic catalyst for initiation of lipid peroxidation at sites of inflammation. *Journal of Biological Chemistry.* 277:46116-46122). Low density lipoprotein (LDL; 1.019<d<1.063 g/ml fraction) and high density lipoprotein (HDL; 1.063<d<1.21 g/ml fraction) were isolated from fresh plasma by sequential ultracentrifugation (Hatch, F. T. 1968. Practical methods for plasma lipoprotein analysis. *Advances in Lipid Research* 6:1-68). Final preparations were extensively dialyzed against 50 mM sodium phosphate (pH 7.0), 200 μM diethylenetriaminepentaacetic acid (DTPA) and stored under N$_2$ until use. LDL was acetylated with acetic acid anhydride (Goldstein, J. L., Ho, Y. K., Basu, S. K., and Brown, M. S. 1979. Binding site on macrophages that mediates uptake and degradation of acetylated low density lipoprotein, producing massive cholesterol deposition. *Proceedings of the National Academy of Sciences of the United States of America.* 76:333-337). NO$_2$Tyr immunostaining was performed as described (MacPherson, J. C., Comhair, S. A., Erzurum, S. C., Klein, D. F., Lipscomb, M. F., Kavuru, M. S., Samoszuk, M. K., and Hazen, S. L. 2001. Eosinophils are a major source of nitric oxide-derived oxidants in severe asthma: characterization of pathways available to eosinophils for generating reactive nitrogen species. *Journal of Immunology.* 166:5763-5772). Specificity of immunostaining for NO$_2$Tyr was confirmed by showing loss of staining (i) in competition studies with 10 mM nitrotyrosine present during antibody—antigen incubations; and (ii) upon reduction of sample with dithionite.

Clinical Specimens—Serum.

For studies involving mass spectrometry-dependent quantification of serum total protein, apoA-I and apoB-100 contents of NO$_2$Tyr and ClTyr, sequential patients (n=45) with cardiovascular disease (CVD) receiving care from the Preventive Cardiology Clinic of the Cleveland Clinic Foundation and healthy volunteers (n=45) responding to advertisements were enrolled. CVD was defined clinically as coronary artery disease, peripheral arterial disease, or cerebral vascular disease. Subjects with CVD were stable and without cardiac symptoms. Patients who experienced a myocardial infarction or stroke within one month preceding enrolment were ineligible. Studies correlating HDL levels of NO$_2$Tyr and ClTyr with ABCA1-dependent cholesterol efflux activities were performed on a separate sequential set of subjects (n=12) without known (CVD) receiving care from the Preventive Cardiology Clinic. All participants gave written informed consent and the Institutional Review Board of the Cleveland Clinic Foundation approved the study protocol. Clinical investigations were conducted in accordance with the Declaration of Helsinki principles. A medical history and record review was performed to define coronary risk factors, including diabetes mellitus (defined by fasting blood glucose >125 mg/dl or hypoglycemic medications), hypertension (blood pressure >140/90 or anti-hypertensive medications in the absence of known cardiac disease), family history of premature coronary heart disease (first degree relative with coronary heart disease prior to age 60 by subject report), history of hypercholesterolemia (fasting LDL cholesterol >160 mg/dl or lipid lowering medications in the absence of known cardiac disease), and cigarette smoking (any smoking within 1 year of study). A fasting blood sample was obtained using a serum separator tube. Serum was isolated, aliquots placed into cryovials supplemented with antioxidant cocktail comprised of butylated hydroxytoluene (100 μM final) and DTPA (2 mM final, pH 7.0), covered in argon and snap frozen at −80° C. until time of analysis.

Immuno-Affinity Purification of Nitrated Proteins.

An ImmunoPure Protein A Orientation Kit (Pierce) was utilized to affinity-purify nitrated proteins from albumin/IgG depleted serum. Briefly, human serum (45 μl) was depleted of albumin and IgG using the ProteoPrep Albumin Depletion Kit (Sigma-Aldrich Corp., St. Louis, Mo.) as recommended by the manufacturer. Affinity purified anti-nitrotyrosine antibody raised against a synthetic octapeptide (Cys-Gly-NO$_2$Tyr-Gly-Gly-Gly-NO$_2$Tyr-Gly) was bound to protein A and cross-linked with dimethylpimelimidate. The albumin/IgG depleted patient serum was diluted in 0.15M NaCl, 0.1M phosphate, pH 7.2, and applied to the column. Unbound protein fractions were eluted with 20 ml of PBS, and 10 ml of 0.5M NaCl. The bound proteins were eluted with 5 mM 3-nitrotyrosine in 0.5M NaCl. The bound fractions were concentrated using Centriprep filter devices (YM-10, Millipore), dialyzed against 0.1M urea, and dried down to a small volume using a Savant Instrument SpeedVac Concentrator (Savant Instruments Inc., Holbrook, N.Y.). Protein in the fractions was monitored with the bicinchoninic acid assay (Pierce), using BSA as standard.

2D SDS-PAGE.

After dialysis, approximately 50 μg of protein was added to 155 μl sample rehydration buffer and absorbed overnight onto 7 cm pH 3-10 non-linear IPG ZOOM strips (Invitrogen). Isoelectric focusing was carried out using the ZOOM IPG runner system from Invitrogen and the Biorad 3000V power supply using the following voltage step protocol: 100 V for 30 min, 200 V for 20 min, 450 V for 15 min, 750 V for 15 min, and 2000 V for 30 min. For the second dimension, focused IPG strips were equilibrated in LDS sample buffer (Invitrogen) in the presence of NUPAGE sample reducing agent (Invitrogen) for 15 min, and an additional incubation in LDS sample buffer in the presence of 125 mM iodoacetamide for 15 min. The strips were placed on 4-12% bis-tris gels and embedded in 0.5% agarose (w/v). The gels were stained for protein using either colloidal blue or silver staining. For immunoblotting gels were transferred to 0.2 μm Immun-Blot PVDF membranes (Bio-Rad, Hercules, Calif.).

Clinical Specimens—Tissue.

LDL-like and HDL-like particles were isolated from atherosclerotic lesions from aortas and femoral artery tissues obtained at autopsy (tissue harvest within 10 h of death). Control studies to confirm that post mortem artifacts were not significant utilized vascular tissues (n=5) obtained fresh at the time of vascular surgery. Normal human aortic tissues were obtained from transplant donors. All tissues were immediately rinsed in ice-cold phosphate buffered saline supplemented with 100 μM DTPA and immediately frozen in Buffer A (65 mM sodium phosphate, pH 7.4, 100 μM DTPA, 100 μM butylated hydroxy toluene), under N$_2$ at −80° C. until analysis.

LDL- and HDL-Like Particle Isolation and Characterization from Normal Human Aortic Tissues and Human Atherosclerotic Lesions.

LDL- and HDL-like particles were isolated from fatty streaks and intermediate lesions of human thoracic aortae by sequential density ultracentrifugation (d=1.019-1.070 g/ml fraction for "lesion LDL", 1.063-1.21 g/ml fraction for "lesion HDL") using a modification of the method of Steinbrecher and Lougheed (Steinbrecher, U. P., and Lougheed, M. 1992. Scavenger receptor-independent stimulation of cholesterol esterification in macrophages by low density lipoprotein extracted from human aortic intima. *Arteriosclerosis & Thrombosis*. 12:608-625) as described (Krul, E. S., Tang, J., Kettler, T. S., Clouse, R. E., and Schonfeld, G. 1992. Lengths of truncated forms of apolipoprotein B (apoB) determine their intestinal production. *Biochemical & Biophysical Research Communications*. 189:1069-1076). "Control Aortic LDL" and "Control Aortic HDL"-like particles were similarly isolated from residual aortic tissues free of visible atherosclerotic plaque from transplant donors. A metal chelator (100 μM DTPA), myeloperoxidase inhibitor (10 mM 3-aminotriazole), and protease cocktail comprised of PMSF and Sigma protease inhibitor cocktail (catalog No P8340) were included in all solutions used for lipoprotein isolation. Control Aortic and Lesion LDL and HDL were subjected to SDS-PAGE (Laemmli, U.K. 1970. Cleavage of structural proteins during the assembly of the head of bacteriophage T4. *Nature*. 227:680-685) with Western blot analysis using either a rabbit anti-human apoB-100 antiserum (Hazen, S. L., and Heinecke, J. W. 1997. 3-Chlorotyrosine, a specific marker of myeloperoxidase-catalyzed oxidation, is markedly elevated in low density lipoprotein isolated from human atherosclerotic intima. *Journal of Clinical Investigation*. 99:2075-2081), or goat anti-human apoA-I (Biodesign, Saco, Me.), respectively. Analysis of Control Aortic and Lesion LDL-like particles with polyclonal antibody to apoB-100 detected a 500 kDa protein, the mass of intact apolipoprotein B100. As previously noted (Krul, E. S., Tang, J., Kettler, T. S., Clouse, R. E., and Schonfeld, G. 1992. Lengths of truncated forms of apolipoprotein B (apoB) determine their intestinal production. *Biochemical & Biophysical Research Communications*. 189:1069-1076), both aggregated/cross-linked and lower molecular mass forms of immunoreactive protein were also present in LDL-like particles isolated from vascular tissues. Similar Western analyses were performed on Control Aortic and Lesion HDL-like particles using antibodies to apoA-I, confirming the presence of apoA-I. Analysis of Control Aortic and Lesion LDL-like particles by high resolution size exclusion chromatography (tandem Superose 6 and 12 columns; Pharmacia LKB) demonstrated that immunoreactive apoB-100, total cholesterol, and the majority of protein mass exhibited an apparent M$_r$ similar to that of LDL isolated from plasma. Identity of apoA-I as a major protein constituent present in Control Aortic and Lesion HDL-like particle preparations was also achieved by tandem MS sequence analysis following excision from Coomassie blue stained SDS PAGE gels.

Several control experiments indicated that post-mortem changes were unlikely to contribute to apoA-I nitration and chlorination. First, control studies were performed on fresh arterial tissues harvested at time of vascular surgery (for lesion) and organ harvest for transplantation (for normal/nonlesion arterial tissues). Comparable levels of $NO_2Tyr$ and ClTyr were noted within these freshly harvested vascular tissues, compared to those obtained at autopsy. Second, following generation of powdered aortic tissues using a stainless steel mortar and pestle at liquid nitrogen temperatures, incubation of aortic tissue powder (suspended in PBS) with MPO (100 nM) for 10 h at room temperature failed to increase levels of $NO_2Tyr$ or ClTyr, as monitored by both mass spectrometry and SDS-PAGE and Western analyses (for $NO_2Tyr$). Third, control studies demonstrated no significant formation of 3-[$^{13}C_6$]ClTyr or 3-[$^{13}C_6$]$NO_2Tyr$ in the above aortic tissue powder/MPO mixtures supplemented with L-[$^{13}C_6$]tyrosine, incubated at room temperature for 10 h, and then subjected to mass spectrometry analysis.

Protein Identification by Mass Spectrometry.

Protein identifications were carried out as previously described (Kinter, M., and Sherman, N. 2000. *Protein Sequencing and Identification Using Tandem Mass Spectrometry*, Willard, B. B., Ruse, C. I., Keightley, J. A., Bond, M., and Kinter, M. 2003. Site-specific quantitation of protein nitration using liquid chromatography/tandem mass spectrometry. *Analytical Chemistry*. 75:2370-2376). Briefly, bands were cut from Coomassie blue stained SDS-PAGE gels, reduced with DTT and alkylated with iodoacetamide. Protein was then digested in-gel by adding trypsin, peptides extracted, and then analyzed by capillary column HPLC-tandem mass spectrometry on an LCQDeca ion trap mass spectrometer system (ThermoFinnigan, San Jose, Calif.) equipped with a nanospray ionization source at a flow rate of 200 nL/min. Digest peptides were separated by reversed-phase capillary HPLC using a 50-µm-i.d. column with a 10-µm tip purchased from New Objective Corp. (Woburn, Mass.). The column was packed with ~6 cm of C18 packing material (Phenomenex, Torrence, Calif.) and eluted using a 45-min gradient of increasing acetonitrile (2-70%) in 50 mM acetic acid. Protein identification was performed using a data-dependent analysis that acquired both mass spectra and CID spectra in a single run (Kinter, M., and Sherman, N. 2000. *Protein Sequencing and Identification Using Tandem Mass Spectrometry*, Willard, B. B., Ruse, C. I., Keightley, J. A., Bond, M., and Kinter, M. 2003. Site-specific quantitation of protein nitration using liquid chromatography/tandem mass spectrometry. *Analytical Chemistry*. 75:2370-2376). The search programs Sequest and Mascot were used for protein identifications. Manual sequence analyses were performed on select deuterium-enriched peptides during hydrogen-deuterium exchange mass spectrometry.

Nitrotyrosine and Chlorotyrosine Analyses

Protein-bound nitrotyrosine and chlorotyrosine were quantified by stable isotope dilution liquid chromatography-tandem mass spectrometry (Brennan, M. L., Wu, W., Fu, X., Shen, Z., Song, W., Frost, H., Vadseth, C., Narine, L., Lenkiewicz, E., Borchers, M. T., et al. 2002. A tale of two controversies: defining both the role of peroxidases in nitrotyrosine formation in vivo using eosinophil peroxidase and myeloperoxidase-deficient mice, and the nature of peroxidase-generated reactive nitrogen species. *Journal of Biological Chemistry*. 277:17415-17427) on a triple quadrupole mass spectrometer (API 4000, Applied Biosystems, Foster City, Calif.) interfaced to a Cohesive Technologies Aria LX Series HPLC multiplexing system (Franklin, Mass.). Synthetic [$^{13}C_6$]-labeled standards were added to samples (either aliquots of serum, tissue/lesion homogenates, or bands visualized on PVDF membranes by colloidal blue stain and then excised) and used as internal standards for quantification of natural abundance analytes. Simultaneously, a universal labeled precursor amino acid, [$^{13}C_9$, $^{15}N_1$]tyrosine, was added. Proteins were hydrolyzed under argon atmosphere in methane sulfonic acid, and then samples passed over mini solid-phase C18 extraction columns (Supelclean LC-C18-SPE minicolumn; 3 ml; Supelco, Inc., Bellefone, Pa.) prior to mass spectrometry analysis. Results are normalized to the content of the precursor amino acid tyrosine, which was monitored within the same injection. Intrapreparative formation of both nitro[$^{13}C_9$, $^{15}N$]tyrosine and chloro[$^{13}C_9$, $^{15}N$]tyrosine was routinely monitored and negligible (i.e. <5% of the level of the natural abundance product observed) under the conditions employed.

Statistical Analysis.

Power calculations were performed based on previously reported means and standard deviations of $NO_2Tyr$ and ClTyr in clinical studies. It was determined that at least 30 patients were needed in each group to have 80% power to detect a 40%.

Example 1

Identification of Apolipoprotein A-I as a Nitrated Protein in Serum

Serum levels of protein-bound nitrotyrosine serve as a predictor of atherosclerotic risk and burden in subjects (Shishehbor, M. H., Aviles, R. J., Brennan, M. L., Fu, X., Goormastic, M., Pearce, G. L., Gokce, N., Keaney, J. F., Jr., Penn, M. S., Sprecher, D. L., et al. 2003. Association of nitrotyrosine levels with cardiovascular disease and modulation by statin therapy. *JAMA*. 289:1675-1680), raising the question of whether nitration of specific proteins might contribute to the atherosclerotic process. As a first step in investigating this question, we sought to determine the identities of nitrated proteins in serum. Samples from patients with CVD and controls were analyzed by SDS-PAGE and visualized by both Western blot analysis using anti-nitrotyrosine antibodies, and Coomassie blue staining for proteins. Comparison of the pattern of immunoreactivity seen in a Western blot vs. protein staining revealed that not all serum proteins are equally nitrated. An example of a disparity between a modest abundance vs. an extensive degree of nitration was reproducibly observed in a 29 kDa protein. This protein band was cut from the Coomassie blue-stained gel, digested with trypsin, and unequivocally identified as apoA-I (NCBI accession number 253362) based upon the detection and sequencing of >30 peptides covering 96% of the protein sequence. Further confirmation of the identity of apoA-I as a nitrated protein was obtained through passage of serum through a column comprised of immobilized antibodies to nitrotyrosine, washing the column with high salt, followed by elution with high salt supplemented with 5 mM nitrotyrosine. Analysis of samples by 2-dimensional SDS-PAGE and capillary LC-tandem mass spectrometry-based sequencing confirmed apoA-I as a recovered protein (>90% coverage by LC/ESI/MS/MS). Further examination of the anti-nitrotyrosine column eluent (high salt+5 mM nitrotyrosine) by 2-D SDS-PAGE followed by Western blot analysis using antibodies to apoA-I provided additional complementary evidence of apoA-I as a nitrated protein in vivo.

Example 2

Demonstration of Apolipoprotein A-I as a Preferred Target of Nitration and Chlorination within Serum, as Well as in Subjects with Versus without Cardiovascular Disease Given the plethora of targets within tissues like serum and the relatively short diffusion distance for a reactive nitrogen species in complex biological matrices, the apparent selective nitration of apoA-I amongst serum proteins strongly suggested the existence of an enzymatic source for NO-derived oxidants in close proximity to the lipoprotein in vivo. One likely candidate was the enzyme MPO, since recent studies have shown this enzyme both capable of catalyzing protein nitration in vivo (Brennan, M. L., Wu, W., Fu, X., Shen, Z., Song, W., Frost, H., Vadseth, C., Narine, L., Lenkiewicz, E., Borchers, M. T., et al. 2002. A tale of two controversies: defining both the role of peroxidases in nitrotyrosine formation in vivo using eosinophil peroxidase and myeloperoxidase-deficient mice, and the nature of peroxidase-generated reactive nitrogen species. *Journal of Biological Chemistry.* 277:17415-17427, Zhang, R., Brennan, M. L., Shen, Z., MacPherson, J. C., Schmitt, D., Molenda, C. E., and Hazen, S. L. 2002. Myeloperoxidase functions as a major enzymatic catalyst for initiation of lipid peroxidation at sites of inflammation. *Journal of Biological Chemistry.* 277:4611646122, Baldus, S., Eiserich, J. P., Mani, A., Castro, L., Figueroa, M., Chumley, P., Ma, W., Tousson, A., White, C. R., Bullard, D. C., et al. 2001. Endothelial transcytosis of myeloperoxidase confers specificity to vascular ECM proteins as targets of tyrosine nitration. *Journal of Clinical Investigation.* 108: 1759-1770, Gaut, J. P., Byun, J., Tran, H. D., Lauber, W. M., Carroll, J. A., Hotchkiss, R. S., Belaaouaj, A., and Heinecke, J. W. 2002. Myeloperoxidase produces nitrating oxidants in vivo. *Journal of Clinical Investigation.* 109:1311-1319), as well as playing a dominant role in generation of NO-derived oxidants under certain circumstances, such as within the extracellular compartment at sites of inflammation (Brennan, M. L., Wu, W., Fu, X., Shen, Z., Song, W., Frost, H., Vadseth, C., Narine, L., Lenkiewicz, E., Borchers, M. T., et al. 2002. A tale of two controversies: defining both the role of peroxidases in nitrotyrosine formation in vivo using eosinophil peroxidase and myeloperoxidase-deficient mice, and the nature of peroxidase-generated reactive nitrogen species. *Journal of Biological Chemistry.* 277:17415-17427). In order to both test the hypothesis that MPO serves as a possible enzymatic catalyst for selective apoA-I nitration in vivo, as well as quantitatively assess whether apoA-I is nitrated to a greater extent within subjects with CVD, sequential patients presenting to a cardiology clinic with documented CVD (n=45) and healthy control subjects (n=44) were consented and their serum samples collected for analysis. The contents of both $NO_2Tyr$ and ClTyr were simultaneously quantified within total serum proteins, isolated apoA-I and isolated apoB-100 utilizing stable isotope dilution HPLC with on-line electrospray ionization tandem mass spectrometry (LC/ESI/MS/MS). Table 2 lists the clinical and laboratory characteristics of the subjects examined. As anticipated, patients with CVD were more likely to have known CVD risk factors including history of diabetes, hypertension, smoking, family history of CVD, and history of hyperlipidemia. Subjects with CVD also had lower LDL cholesterol levels and were more likely to be on statin therapy, features likely attributable to ascertainment bias from enrollment of CVD subjects in a cardiology clinic.

TABLE 2

Clinical and laboratory characteristics

|  | Controls (n = 44) | CVD (n = 45) | p value |
|---|---|---|---|
| Age | 44.3 ± 11.1 | 65.6 ± 8.5 | <0.001 |
| Male gender (%) | 24 (54.6) | 17 (37.8) | 0.12 |
| Diabetes (%) | 0 (0) | 24 (53.3) | <0.001 |
| Hypertension (%) | 14 (31.8) | 32 (71.1) | <0.001 |
| Smoking (%) | 22 (50.0) | 37 (82.2) | 0.001 |
| Family hx CVD (%) | 5 (11.4) | 19 (42.2) | 0.001 |
| Hx hyperlipidemia (%) | 7 (15.9) | 31 (68.9) | <0.001 |
| Statin use | 0 (0) | 28 (62.2) | <0.001 |
| TC (mg/dL) | 201 ± 33 | 165 ± 36 | <0.001 |
| HDLc (mg/dL) | 60 ± 16 | 42 ± 15 | <0.001 |
| LDLc (mg/dL) | 120 ± 34 | 91 ± 24 | <0.001 |
| TG (mg/dL) | 108 ± 54 | 171 ± 96 | <0.001 |
| Fasting Glucose (mg/dL) | 93 ± 13 | 94 ± 3 | 0.43 |

Data are presented as either percent or mean ± standard deviation as indicated.

CVD = cardiovascular disease; HDLc = high density lipoprotein cholesterol; Hx = history of; LDLc = low density lipoprotein cholesterol; TC = total cholesterol; TG = triglyceride.

Consistent with our recent published studies (Shishehbor, M. H., Aviles, R. J., Brennan, M. L., Fu, X., Goormastic, M., Pearce, G. L., Gokce, N., Keaney, J. F., Jr., Penn, M. S., Sprecher, D. L., et al. 2003. Association of nitrotyrosine levels with cardiovascular disease and modulation by statin therapy. *JAMA.* 289:1675-1680), serum $NO_2Tyr$ content was significantly increased approximately 1.5-fold (p<0.001) in subjects with CVD relative to that of healthy controls (Table 3). Similar results (2-fold increase; p=0.001 for CVD vs. controls, Table 3) were observed when analyzing the $NO_2Tyr$ content of isolated apoB-100, the major protein constituent of LDL and a lipoprotein reported to bind to MPO in vitro (Carr, A. C., Myzak, M. C., Stocker, R., McCall, M. R., and Frei, B. 2000. Myeloperoxidase binds to low-density lipoprotein: potential implications for atherosclerosis. *FEBS Letters.* 487: 176-180, Yang, C. Y., Gu, Z. W., Yang, M., Lin, S. N., Garcia-Prats, A. J., Rogers, L. K., Welty, S. E., and Smith, C. V. 1999. Selective modification of apoB-100 in the oxidation of low density lipoproteins by myeloperoxidase in vitro. *Journal of Lipid Research.* 40:686-698). Remarkably, a 70-fold enrichment in $NO_2Tyr$ content was noted within serum apoA-I relative to serum total proteins and isolated apoB-100. Moreover, a significant increase in $NO_2Tyr$ content of apoA-I was also noted in serum from CVD vs. healthy control subjects (p=0.005; Table 2). Parallel analyses of samples for ClTyr content, a protein modification specific for MPO-catalyzed oxidation (Hazen, S. L., Hsu, F. F., Gaut, J. P., Crowley, J. R., and Heinecke, J. W. 1999. Modification of proteins and lipids by myeloperoxidase. *Methods in Enzymology* 300:88-105, Brennan, M. L., Wu, W., Fu, X., Shen, Z., Song, W., Frost, H., Vadseth, C., Narine, L., Lenkiewicz, E., Borchers, M. T., et al. 2002. A tale of two controversies: defining both the role of peroxidases in nitrotyrosine formation in vivo using eosinophil peroxidase and myeloperoxidase-deficient mice, and the nature of peroxidase-generated reactive nitrogen species. *Journal of Biological Chemistry.* 277:17415-17427, Hazen, S. L., and Heinecke, J. W. 1997. 3-Chlorotyrosine, a specific marker of myeloperoxidase-catalyzed oxidation, is markedly elevated in low density lipoprotein isolated from human atherosclerotic intima. *Journal of Clinical Investigation.* 99:2075-2081, Brennan, M. L., Anderson, M., Shih, D., Qu, X., Wang, X., Mehta, A., Lim, L., Shi, W., Hazen, S. L., Jacob, J., Crowley, J., Heinecke, J. W., and Lusis, A. J. 2001. Increased atherosclerosis in myeloperoxidase-deficient mice. *J. Clin. Invest.* 107:419-30), revealed relatively low levels within total proteins and isolated apoB-100 from serum compared to over 100-fold enrichment in ClTyr content noted within isolated apoA-I (Table 2). Further, while trends for increases in ClTyr content within subjects with CVD were noted in total protein and isolated apoB 100, these differences failed to reach statistical significance. In contrast, significant increases in ClTyr content were observed within apoA-I recovered from serum (p<0.001; Table 3).

TABLE 3

Apolipoprotein A-I is a preferred target for nitration and chlorination in serum and in cardiovascular disease

| | Nitrotyrosine | | Chlorotyrosine | |
|---|---|---|---|---|
| | median(IQR) (μmol oxTyr/mol Tyr) | p value | median(IQR) (μmol oxTyr/mol Tyr) | p value |
| Section 1.01 Serum total protein | | | | |
| Control | 6.1 [3.9-7.8] | | 1.6 [0.6-2.4] | |
| CVD | 9.0 [5.7-12.9] | <0.001 | 1.9 [1.3-3.1] | 0.07 |
| apoB-100 | | | | |
| Control | 4.0 [1.3-6.9] | | 0.0 [0.0-1.9] | |
| CVD | 8.7 [5.2-12.1] | 0.001 | 1.9 [0.1-4.0] | 0.24 |
| Section 1.02 apoA-I | | | | |
| Control | 438 [335-598] | | 186 [114-339] | |
| CVD | 629 [431-876] | 0.005 | 500 [335-765] | <0.001 |

Aliquots of serum (100 ug protein) from the entire cohort from Table 2 (CVD and healthy control subjects) were either analyzed directly (for total protein) or resolved by SDS PAGE, transferred to PVDF membranes, and bands corresponding to apoA-I and apoB-100 visualized, excised, and then analyzed by stable isotope dilution LC/ESI/MS/MS, as described under Methods. Results shown are for median and interquartile ranges of nitrotyrosine and chlorotyrosine contents of total serum protein or the indicated lipoprotein, expressed as the mole ratio of oxidized amino acid to parent amino acid, tyrosine. The p values shown are for comparisons of $NO_2Tyr$ and ClTyr content between Control and CVD groups within the corresponding indicated protein(s). apo = apolipoprotein; CVD = cardiovascular disease; IQR = interquartile range.

The strength of the relationship between the content of $NO_2Tyr$ and ClTyr within total proteins and isolated apoA-I from serum was further examined in the entire cohort (CVD plus controls). As shown in Table 4 (top), increasing $NO_2Tyr$ content was associated with increasing frequency of CVD, as monitored in either total serum proteins or isolated apoA-I from serum. Further, comparisons between subjects with higher vs. lower levels of $NO_2Tyr$ (third vs. first tertile) demonstrated approximately 6-fold increase in odds for having CVD, whether examining total proteins or isolated apoA-I from serum (Table 3, bottom). In contrast, only the ClTyr content of isolated apoA-I, and not ClTyr content of total serum proteins (or apoB-100, not shown), was associated with increasing frequency or odds of CVD within the cohort. Remarkably, subjects possessing a high (top tertile) apoA-I ClTyr content were 16-fold more likely to have CVD than those with low (bottom tertile) apoA-I ClTyr content (Table 4, bottom).

TABLE 4

Relationship between serum total protein and apolipoprotein A-I nitrotyrosine and chlorotyrosine content with cardiovascular disease prevalence

| | Frequency of CVD per Tertile | | | |
|---|---|---|---|---|
| | 1 | 2 | 3 | p for trend |
| Serum | | | | |
| Total protein $NO_2Tyr$ | 30.8% | 33.3% | 69.2% | 0.005 |
| apoA-I $NO_2Tyr$ | 32.0% | 44.0% | 72.0% | 0.005 |
| 1. total protein ClTyr | 40.0% | 50.0% | 58.3% | 0.20 |
| apoA-I ClTyr | 20.0% | 48.0% | 80.0% | <0.001 |

| | Odds Ratio (95% CI) of CVD per Tertile | | |
|---|---|---|---|
| | 1 | 2 | 3 |
| Serum | | | |
| Total protein $NO_2Tyr$ | 1.0 | 1.1 (0.4-3.6) | 5.1 (1.6-16.4) |
| apoA-I $NO_2Tyr$ | 1.0 | 1.7 (0.5-5.3) | 5.5 (1.6-18.4) |
| 2. total protein ClTyr | 1.0 | 1.5 (0.5-4.6) | 2.1 (0.7-6.6) |
| apoA-I ClTyr | 1.0 | 3.7 (1.1-13.0) | 16.0 (4.0-64.0) |

Displayed are (top) frequencies of cardiovascular disease prevalence within each tertile of the entire cohort; and (bottom) odds ratios and 95% confidence intervals for second and third tertiles compared to the lowest (first) tertile as predictors of CVD.
apo = apolipoprotein; CI = confidence interval; ClTyr = chlorotyrosine; CVD = cardiovascular disease; $NO_2Tyr$ = nitrotyrosine.

Example 3

Demonstration of Apolipoprotein A-I as a Preferred Target of Nitration and Chlorination within Human Atherosclerotic Lesions To examine whether the preferential targeting of apoA-I by NO⁻ and MPO-generated oxidants occurred within human atheroma, additional studies were performed examining total proteins, apoB-100 and apoA-I recovered from human aortic tissues. LDL-tike and HDL-like particles were isolated from both normal aortic tissues and atherosclerotic tissues by differential buoyant density centrifugation, and then confirmed to be enriched both in cholesterol and the appropriate apolipoprotein preparation by Western analyses using polyclonal antibodies to either apoB-100 or apoA-I, as described under "Methods". The majority of apoA-I recovered within HDL-like particles from atherosclerotic lesions was monomeric. More quantitative assessments of $NO_2Tyr$ and ClTyr contents of apoA-I recovered from normal aortic and lesion tissues relative to that observed in aortic and lesion total proteins and apoB-100 were obtained by stable isotope dilution LC/ESI/MS/MS analyses, the results for which are shown in Table 4. Of note, the contents of $NO_2Tyr$ and ClTyr within total proteins, apoB-100 and apoA-I recovered from normal aortic tissues and human atherosclerotic lesions were higher than that observed in serum (compare Tables 3 versus 5), suggesting protein modification by NO— and MPO-generated oxidants preferentially occurs within the artery wall, particularly within atherosclerotic lesions, compared to the intra-vascular (blood) compartment. As was observed within serum and the serum-derived isolated lipoproteins, the contents of both $NO_2Tyr$ and ClTyr in lesion apoA-I demonstrated a dramatic selective enrichment relative to lesion total proteins and lesion apoB-100 (Table 5). Similarly, higher levels are observed within total proteins and the isolated lipoproteins from diseased vs. normal vascular tissues.

TABLE 5

Apolipoprotein A-I is a preferred target for nitration and chlorination within human aortic atherosclerotic lesions

| | Nitrotyrosine | | Chlorotyrosine | |
|---|---|---|---|---|
| | Median(IQR) (μmol oxTyr/mol Tyr) | p value | Median(IQR) (μmol oxTyr/mol Tyr) | p value |
| Section 1.03 ormal total protein | 55 [24-143] | | 63 [25-128] | |
| apoB-100 | 97 [43-222] | 0.57 | 49 [21-121] | 0.93 |
| Section 1.04 poA-I | 401 [185-637] | <0.001 | 678 [299-1,311] | <0.001 |
| Section 1.05 esion total protein | 108 [51-346] | | 232 [111-431] | |
| apoB-100 | 255 [91-480] | 0.67 | 318 [59-385] | 0.92 |
| Section 1.06 poA-I | 2,340 [1,665-5,050] * | <0.001 | 3,930 [1,679-7,005] * | <0.001 |

Specimens of normal human aorta (n = 10 subjects) and human aortic atherosclerotic tissues (n = 22 subjects) were stripped of adventia, and then, pulverized into a powder in stainless steel mortar and pestle at liquid nitrogen temperatures, and the contents of nitrotyrosine and chlorotyrosine analyzed by stable isotope dilution LC/ESI/MS/MS, as described under Methods. Total protein content of biomarkers was ascertained using powdered human vascular tissue. The contents of oxidized amino acids within normal aortic and atherosclerotic lesion-derived apoB-100 and apoA-I were assessed following isolation of LDL-like and HDL-like particles from powdered vascular tissues by sequential buoyant density centrifugation, further resolving by SDS PAGE, transfer to PVDF membranes, and then bands corresponding to apoA-I and apoB-100 visualized, excised, and analyzed by stable isotope dilution LC/ESI/MS/MS, as described under Methods. Results shown are for median and interquartile ranges of nitrotyrosine and chlorotyrosine contents of normal aortic and lesion total protein or the indicated lipoproteins, expressed as the mole ratio of oxidized to parent amino acid, tyrosine. The p values shown are for comparisons of nitrotyrosine or chlorotyrosine content in the indicated isolated lipoproteins from human normal aortic and atherosclerotic lesions vs. the corresponding content observed in normal or lesion aortic tissue total proteins. * P < 0.001 for comparison of lesional apoA-I versus normal aortic tissue apoA-I.

The present studies provide both the first direct evidence of apoA-I, the major protein constituent of HDL, as a preferential target for nitration and chlorination in the artery wall, as well as a potential mechanism(s) for generation of a pro-atherogenic form of HDL. The remarkable selective enrichment in apoA-I $NO_2Tyr$ and ClTyr content observed both within human atherosclerotic lesions and the systemic circulation indicate that NO-derived oxidants and MPO-catalyzed reactions selectively target the lipoprotein for oxidative modification. We observed a combined ox-amino acid (ox-AA) content of 5,500 μmol ox-AA/mol Tyr within lesional apoA-I (Table 5). Given there are 7 tyrosine residues per apoA-I and up to 4 apoA-I molecules per HDL particle, we calculate that on average, approximately 15% of the HDL-like particles recovered from human aortic lesions possess at least one oxidative modification (i.e. 5.5 ox-AA/$10^3$ Tyr×7 Tyr/apoA-1×4 apoA-I/HDL particle=15.4%). If one looks a the top quartile values, which demonstrated a combined ox-AA content ranging between 10,000 to 25,000 μmol ox-AA/mol Tyr, then a remarkable 28% to 50% of lesional HDL in this top quartile possess either a ClTyr or a $NO_2Tyr$ residue. Since MPO, HOCl-modified proteins, and apoA-I all co-localize within the protected environment of the subendothelial compartment, it is not hard to imagine that this number may be even higher in some locations. While the selective enrichment of MPO-generated oxidation products was most pronounced within circulating HDL of individuals with CVD and human atherosclerotic lesions, marked enrichment was also noted within apoA-I recovered from both serum of healthy subjects and transplant donor aortic tissues, suggesting a potential physiologic anti-inflammatory/anti-oxidant role for apoA-I binding of MPO and scavenging of MPO-generated oxidants.

B. apoA-I Peptide Fragment Studies

The present studies establish the molecular events associated with MPO-mediated modification of apoA-I and specifically relate those events to alterations of apoA-I function. We have mapped the sites of MPO-mediated nitration and chlorination with tandem mass spectrometry and now demonstrate the specific modification of two regions of the protein. We also establish the hierarchy of modifications and report a colocalization of the preferred residue modified by both MPO-catalyzed chlorination and nitration with the MPO-interaction site in the helix 8 region. A strong correlation is noted between dose-dependent progression of MPO-mediated site-specific modifications of apoA-I and loss of both ABCA1-dependent reverse cholesterol transport and inhibition of apoA-I lipid binding. Our data suggest a link between the degree of MPO-catalyzed site-specific apoA-I modifications and the loss of important anti-atherosclerotic functions of HDL. MPO-catalyzed oxidative modification of apoA-I in the artery wall may thus contribute to the clinical association between MPO and cardiovascular disease.

Experimental Procedures

HDL and apoA-I Modification Reactions.

Whole blood was drawn from healthy donors who gave written informed consent for a study protocol approved by the Institutional review board of the Cleveland Clinic Foundation. HDL was isolated from human plasma (density range-1.063 g/mL to 1.210 g/mL) using differential ultra-centrifugation and extensively dialyzed in 50 mM phosphate buffer (pH 7.0) with 100 μM diethylenetriamine pentaacetic acid (DTPA) in the dark at 4° C. Delipidated and purified apoA-I was purchased from Biodesign International (Saco, Me.) and used without further purification.

The MPO-mediated modification reactions were carried out in a 50 mM phosphate buffer, pH 7.0, containing 100 μM DTPA, 1 mg/mL protein (apoA-I), 57 nM purified human MPO (donor: hydrogen peroxide, oxidoreductase, EC 1.11.1.7; $A_{430}/A_{280}$ ratio of 0.79), and either 1 mM nitrite (for the nitration reactions) or 100 mM chloride (for the chlorination reactions). The myeloperoxidase reactions were initiated by adding hydrogen peroxide at varying concentrations (0-200 μM) and carried out at 37° C. for 1 h. These reaction conditions include physiologically relevant amounts of MPO, chloride and nitrite, and hydrogen peroxide concentrations that range from physiologic to pathologic.

The peroxynitrite and HOCl reactions were similarly carried out at 37° C. for 1 h in 50 mM phosphate buffer, pH 7.0, containing 100 μM DTPA with the peroxynitrite and HOCl added to give final concentrations between 0 and 200 μM.

In all reactions, the concentrations of the key reactants was verified spectrophotometrically using molar extinction coefficients of 170 $cm^{-1}mM^{-1}$ at 430 nm for MPO, 39.4 $cm^{-1}M^{-1}$ at 240 nm for hydrogen peroxide, 350 cm$^{-1}$M$^{-1}$ at 292 nm for HOCl (NaOCl), and 1670 cm$^{-1}$M$^{-1}$ at 302 nm for peroxynitrite.

The modified proteins were taken immediately for the apoA-I functional studies described below. An aliquot of each reaction was removed, precipitated with acetone, and separated by SDS-PAGE for the mass spectrometry experiments.

Mass Spectrometry Experiments.

Protein Digestion.

The protein bands were digested according to an in-gel digestion procedure (Kinter, M., and Sherman, N.E. (2000) *Protein Sequencing and Identification Using Tandem Mass Spectrometry*. John Wiley and Sons, New York). Briefly, the protein bands were cut from the gel and washed in 50% ethanol/5% acetic acid prior to tryptic digestion with a modified, sequencing grade trypsin (Promega, Madison, Wis.) overnight at room temperature. The peptides were extracted from the gel, evaporated to dryness, and reconstituted in either 1% acetic acid or 0.1% formic acid for analysis by capillary column HPLC-electrospray ionization mass spectrometry.

Identification of the Modification Sites.

The detailed mapping and detection of the nitration and chlorination sites was carried out using an LCQ Deca ion trap mass spectrometer system (ThermoFinnigan, San Jose, Calif.) equipped with a nanospray ionization source (Protana, Odense, Denmark). The source was operated under microspray conditions at a flow rate of 200 n/min. The digests were analyzed by reversed-phase capillary HPLC using a 50-µm i.d. column with a 15-µm i.d. tip purchased from New Objective Corp. (Woburn, Mass.). The column was packed with ~6 cm of C18 packing material (Phenomenex, Torrence, Calif.) and eluted using a 45-min gradient of increasing acetonitrile (2-70%) in 50 mM acetic acid. The data were acquired in the data-dependent mode, recording a mass spectrum and three collision-induced dissociation (CID) spectra in repetitive cycles (Kinter, M., and Sherman, N.E. (2000) *Protein Sequencing and Identification Using Tandem Mass Spectrometry*. John Wiley and Sons, New York). The program Sequest was used to compare all CID spectra recorded to the sequence of human apoA-1 (NCBI accession number 229513) and considering the appropriate changes in the tyrosine residues masses of +34 Da for chlorination and +45 Da for nitration.

Site-Specific Quantitation of Protein Modification.

Site-specific quantitation experiments were performed on a QToFmicro mass spectrometry system (Waters, Milford, Mass.) equipped with a CapLC HPLC system (Waters) with autoinjector. The electrospray ionization source was operated under microspray conditions at a flow rate of 600 nL/min. The digests were analyzed by reversed-phase capillary HPLC using a 75-µm i.d. column with a 19-µm i.d. nanospray source capillary. The column was packed with ~15 cm of 10-µm C18 packing material (Phenomenex, Torrence, Calif.) and eluted using a 45-min gradient of increasing acetonitrile (2-70%) in 0.1% formic acid. Quantitation was achieved by using the Native Reference Peptide method developed for the site-specific quantitation of post-translational modifications (38, 39) in the selected ion monitoring mode (SIM). For the SIM experiments, full scans from m/z 300 to m/z 1600 were acquired with the time-of-flight mass analyzer of the QToF instrument and mass chromatograms constructed based the m/z value of the different peptide ions of interest. The apoA-I peptides ATEHLSTLSEK, SEQ ID NO. 9, and QGLLPV-LESFK, SEQ ID NO. 10 were used as native reference peptides. The relative quantity of the each analyte peptide was determined by dividing the chromatographic peak area of that analyte peptide by the chromatographic peak area of the reference peptide.

ApoA-I Functional Studies.

Cholesterol Efflux.

The cholesterol efflux experiments were performed according to established procedures (Smith, J. D., Miyata, M., Ginsberg, M., Grigaux, C., Shmookler, E., and Plump, A. S. (1996) J. Biol. Chem. 271, 30647-30655, Takahashi, Y., and Smith, J. D. (1999) Proc. Natl. Acad. Sci. U.S.A. 96, 11358-11363). Subconfluent RAW264.7 cells in 24-well dishes were cholesterol loaded and labeled overnight in 0.5 mL of DGGB (DMEM supplemented with 50 mM glucose, 2 mM glutamine, and 0.2% BSA), containing [$^3$H]-cholesterol-labeled acetylated low density lipoprotein (AcLDL). The [$^3$H]-cholesterol-labeled AcLDL was prepared by incubating [$^3$H]-cholesterol for 30 min at 37° C. with the AcLDL and diluted in DGGB to give a final concentration of 50 µg/ml AcLDL with 0.33 µCi/ml [$^3$H]-cholesterol. The day after labeling, the cells were washed three times in PBS, 0.2% BSA and incubated with 0.5 mL of DGGB with or without 0.1 mM 8-Br-cAMP for 16 h. After the 16-h incubation, 50 µg/mL of HDL protein in 0.5 mL DGGB with or without 8-Br-cAMP was added to each well. After a 4-h incubation at 37° C., 100 µL of medium was removed, centrifuged, and the radioactivity counted as a measure of the effluxed cholesterol in the media. The respective cells from each well were extracted with hexane/isopropanol (3:2, v:v) and the radioactivity determined as a measure of the cholesterol retained in the cell. The percentage of cholesterol effluxed was calculated as the radioactivity in the medium divided by the total radioactivity (medium radioactivity plus cell radioactivity).

Lipid Binding.

An LDL aggregation assay was used to test apoA-I lipid binding, modified from a previously described assay (Liu, H., Scraba, D. G., and Ryan, R. O. (1993) FEBS Lett. 316, 27-33). In a 96-well assay plate, 75 µg of LDL was mixed with or without 3 µg of control or modified apoA-I in a final volume of 2001 of reaction buffer (50 mM Tris-HCl, pH 7.4, with 150 mM NaCl and 2 mM CaCl$_2$). Each reaction was performed in triplicate. The plate was then incubated in a SpectraMax plate reader (Molecular Devices, Sunnyvale, Calif.) at 37° C. for 10 min. A 20 µL aliquot of diluted phospholipase C, derived from *Bacillus cereus* (Sigma P7147), sufficient to induce aggregation in 1 hr, or a buffer control, was added to each well to hydrolyze the phospholipid polar head groups to make the LDL surface hydrophobic and initiate aggregation. Aggregation at 37° C. was monitored by absorbance at 478 nm, read every 2 minutes for a period of 1 hr. ApoA-I lipid binding activity results in the inhibition of the LDL aggregation, and was calculated from the aggregation rate (ΔO.D./min.) during the rapid phase that occurred after a short time lag. The aggregation rate for the modified apoA-I was normalized to the rate of native apoA-I.

Detection of Modified apoA-I in Human Atheroma.

ApoA-I Isolation.

Human atheroma tissue was isolated from aortas obtained at autopsy within 10 h of death. The tissue was immediately rinsed in ice-cold phosphate buffered saline supplemented with 100 µM DTPA and immediately frozen in 65 mM sodium phosphate, pH 7.4, with 100 µM DTPA and 100 µM butylated hydroxy toluene, under N$_2$ at −80° C. until analysis.

Fatty streaks and intermediate lesions of human thoracic aorta were powered using a stainless steel mortar and pestle at liquid nitrogen temperatures and mixed with PBS, containing 100 µM DTPA and a protease inhibitor cocktail (Sigma catalog No P8340) for 10 hours at 4° C. The suspended lesion sample was centrifuged and the supernatant used for apoA-I purification. For the purification, apoA-I was bound to an anti-HDL IgY resin (GenWay Biotech, San Diego, Calif.), eluted in 0.1M glycine (pH 2.5), and the eluate neutralized by addition of 1M tris (pH 8.0). The neutralized sample was dissolved in sample loading buffer without heating, run in a 12.5% SDS-PAGE gel (Criterion, BioRad Laboratories), and detected by Coomassie blue-staining. The SDS-PAGE analysis revealed that >90% of the protein recovered from the column was apoA-I.

LC-Tandem MS Analysis.

The immunoaffinity isolated apoA-I band was cut from the gel and digested with trypsin as described above. The LC-tandem MS experiments used a ThermoFinnigan LTQ linear ion trap mass spectrometer with a Surveyor HPLC pump and autosampler system. Samples were injected onto a 10-cm×75 µm i.d. capillary column that was eluted with a linear gradient of acetonitrile in 50 mM acetic acid at approximately 1 µL/min. Selected reaction monitoring experiments (SRM) were used to record the product ion spectra of molecular ion of peptides containing each modified tyrosine residue characterized in the mapping experiments. Chromatograms for those peptides were reconstructed by plotting the fragmentation of the molecular ions to the most abundant product ions in the respective CID spectra. Detection of the appropriate peptide was verified by the CID spectrum that was recorded at that retention time.

Statistical Analyses.

Statistically significant differences were determined by either a one-way analysis of variance using a Tukey-Kramer multiple comparisons test or a Student's t-test. Statistical significant differences are reported when p<0.05.

Example 4

Mapping the Nitration and Chlorination Sites in apoA-I

Initial experiments focused on determining the tyrosine nitration sites in apoA-I produced by treating HDL with both an enzymatic modification system (MPO/$H_2O_2$/$NO_2^-$) with varying concentrations of hydrogen peroxide, and a non-enzymatic system using varying concentrations of peroxynitrite. After each treatment, the proteins in HDL were precipitated with cold acetone, separated by SDS-PAGE, and the apoA-I band cut from the gel for in-gel digestion with trypsin. The digest was analyzed by capillary column HPLC-tandem mass spectrometry using the data-dependent mode of the ion trap mass spectrometry system. Approximately 2000 CID spectra were recorded and these spectra were searched for the spectra of modified peptides. The search routine was focused on the amino acid sequence of apoA-I and used a tyrosine residue mass difference of +45 Da to find the spectra of the nitrated peptides. These analyses detected peptides that covered 95% of the protein sequence, including peptides that contained all 7 of the tyrosine residues in the mature apoA-I sequence. Two peptides containing nitrotyrosine residues (Y192 and Y166) were found in HDL treated with the MPO/$H_2O_2$/$NO_2^-$ at concentrations of hydrogen peroxide <50 µM. At higher hydrogen peroxide concentrations (>100 µM), additional nitrotyrosine-containing peptides (Y29 and Y236) could also be detected. The three remaining tyrosine residues are contained in peptides that were detected and sequenced in these analyses, but no corresponding nitrated form was found under any reaction condition that was tested. As a comparison, a similar reaction of HDL with 100M peroxynitrite gave nitrotyrosine modifications of the apoA-I at three tyrosine residues; Y166, Y18, and Y236. Again, the remaining tyrosine residues were detected in these analyses exclusively in the un-nitrated form.

The CID spectra of the five nitrated peptides are shown in FIG. 1. For each peptide, the identity is established by the series of product ions recorded in the respective CID spectrum. A component of these CID spectra is the characteristic residue mass of the nitrotyrosine moiety (208 Da). Overall, the combination of the peptide molecular weight measurements, the peptide sequence information in the CID spectra, and the known apoA-I amino acid sequence allows unambiguous assignment of the nitrotyrosine positions.

Figure 2:
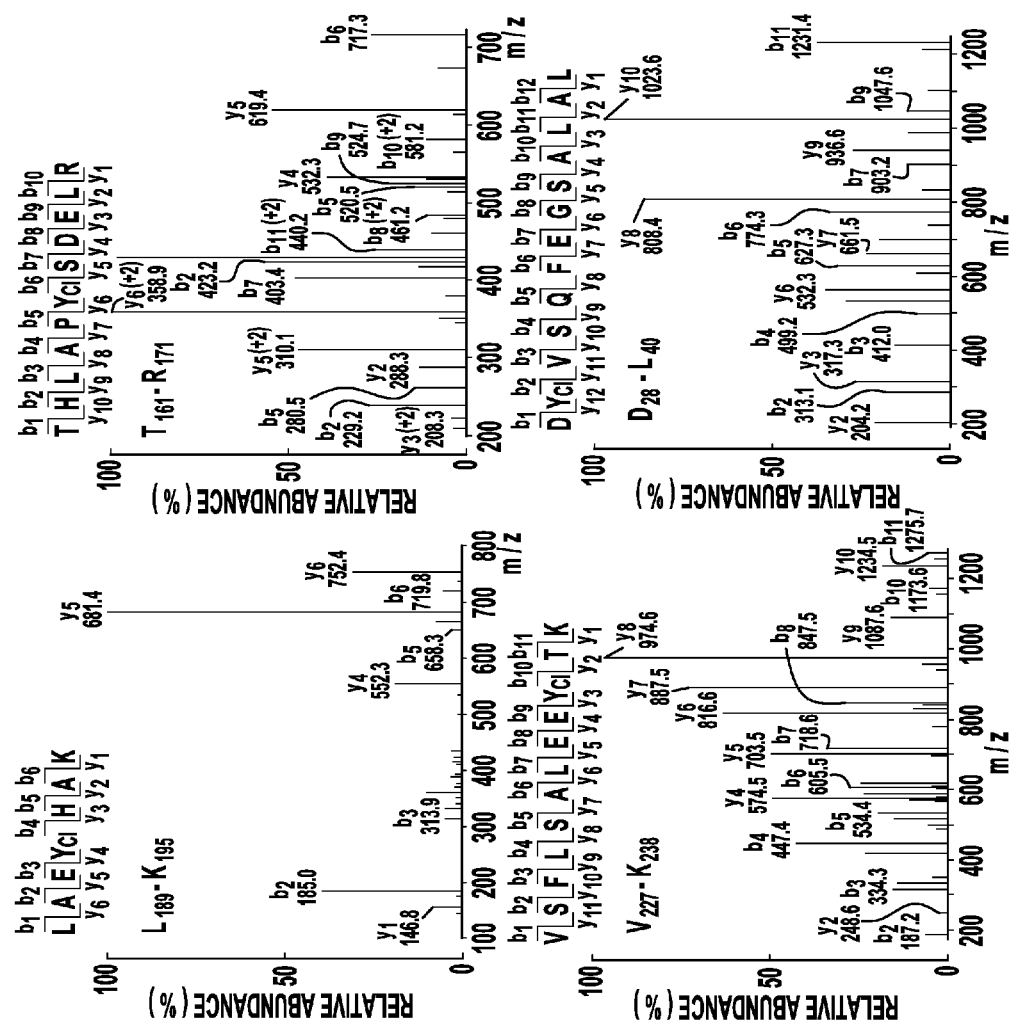
FIG. 2. Collision-induced dissociation (CID) spectra of the chlorotyrosine-containing peptides. The spectra were acquired during the analysis of in-gel tryptic digests of the apoA-I band from HDL treated with either the $MPO/H_2O_2/Cl^-$ protein chlorination system, as described in the methods. Doubly and triply charged ions (as indicated) were detected and fragmented in an LC-tandem MS experiment using an ion trap mass spectrometer system. The same series of peptides were sequenced in both the MPO- and HOCl-mediated reactions.

Subsequent experiments used complementary protein chlorination systems, with both enzymatic (MPO/$H_2O_2$/CY) and non-enzymatic (HOCl) reactions, to modify the HDL. Four sites of chlorination were detected in both of these reactions, Y192, Y166, Y29, and Y236. These are the same tyrosine residues that were nitrated by the MPO/$H_2O_2$/$NO_2^-$ reaction. As noted for the nitration sites, chlorination of Y192 and Y166 was detected at hydrogen peroxide concentrations <50 µM whereas chlorination of Y29 and Y236 required >100 µM hydrogen peroxide. The Y18 nitration site seen with peroxynitrite treatment was not chlorinated by either the MPO- or HOCl-mediated reaction. FIG. 2 contains the CID spectra of the four chlorinated peptides. These CID spectra are characterized by a fragmentation pattern that includes the residue mass of the chlorotyrosine (197 Da for the more abundant $^{35}Cl$ isotope). As note above for the nitrated peptides, the combination of the peptide molecular weight, the information in CID spectrum, and the apoA-I amino acid sequence gives a clear-cut assignment of the chlorotyrosine positions.

Example 5

Quantitative Analyses Identify the Preferred Modification Sites

A comprehensive map of the nitration and chlorination sites in apoA-I is shown in FIG. 3. One observation made during the initial mapping experiments was a potential hierarchy in the various modifications, with two of the MPO-mediated nitration/chlorination sites being modified prior to the other two, one MPO-mediated modification site that was not modified by peroxynitrite, and one peroxynitrite modification site that was not modified by MPO. As a result, quantitative experiments were designed to specifically determine the order of the nitration and chlorination sites.

These quantitative experiments used our previously described Native Peptide Reference method to follow the disappearance of the different regions of apoA-I, represented as the respective tyrosine-containing peptides formed by the trypsin digestion (Willard, B. B., Ruse, C. I., Keightley, J. A., Bond, M., and Kinter, M. (2003) Anal. Chem. 75, 2370-2376, Ruse, C. I., Willard, B., Jin, J. P., Haas, T., Kinter, M., and Bond M. (2002) Anal. Chem. 74, 1658-1664). HDL was treated under nitration or chlorination conditions with increasing amounts of $H_2O_2$ in the MPO-mediated reactions, or increasing amounts of peroxynitrite and HOCl in the non-enzymatic reactions. The reactions were stopped by protein precipitation with −20° C. acetone and separated by SDS-PAGE. The apoA-I bands were cut for tryptic digestion and the digests analyzed by capillary column LC-ESI-MS. The progression of MPO-mediated modification of the individual sites in apoA-I was monitored by plotting mass chromatograms for each tyrosine containing peptide and calculating the respective peak area ratios relative to the unmodified native reference peptide. As shown in FIGS. 4B and 5B, progression of MPO-mediated modification, with increasing concentrations of $H_2O_2$, at each site in apoA-I produces a decreased recovery of the respective unmodified peptides in the digest. These data revealed that Y192 serves as the preferred MPO-catalyzed nitration and chlorination site, followed by Y166 and Y29, and with only a minor degree of modification of Y236 at higher levels of oxidant. A comparable pattern of oxidative modification was also seen in the HOCl reaction. Remarkably, the relative effectiveness of the HOCl reaction was significantly less than that of the MPO-catalyzed chlorination reaction. Specifically, the MPO-catalyzed oxidation reaction produced greater modification at every concentration of $H_2O_2$ examined relative to molar equivalent amounts of HOCl. In contrast, the dose response characteristics of the peroxynitrite reaction differed both in the efficiency of the modification reaction and in the clear preference for nitration of Y18 and the absence of nitration at Y192.

Example 6

Oxidatively Modified apoA-I is Functionally Impaired

Figure 4A:
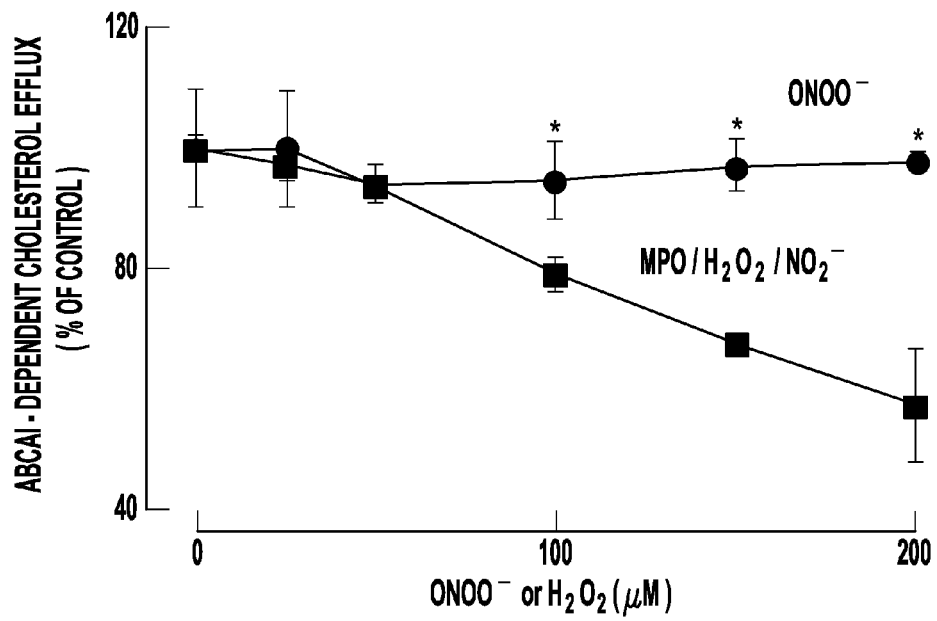
FIG. 4. Dose-dependent apoA-I nitration and the impairment of reverse cholesterol transport activity. HDL was nitrated in a series of either $MPO/H_2O_2/NO_2^-$ reactions with increasing amounts of $H_2O_2$ or peroxynitrite, as indicated, for 1.5 h. A) The effect of the nitration reactions on the ABCA1-dependent reverse cholesterol efflux of the HDL. The modified HDL from each reaction was subsequently incubated with murine RAW264 macrophages loaded with $^3$H-cholesterol-labeled acetylated low density lipoprotein (AcLDL). These cells were treated with the modified HDL in the presence of cAMP to measure the ABCA1-dependent component of reverse cholesterol transport. After 4 hours, media and cellular $^3$H was counted and the percent efflux calculated as the amount of $^3$H-cholesterol in the media divided by the total $^3$H-cholesterol (media+cellular). All values were normalized to the ABCA1-dependent cholesterol efflux obtained with unmodified HDL. B) Site-specific quantitation of apoA-I nitration determined using LC-MS. The proteins in the modified HDL reaction were precipitated with cold acetone, separated by SDS-PAGE, and detected by Coomassie blue staining. The apoA-I was cut from the gel and digested by trypsin. The progression of the nitration reaction was followed quantitatively using the native reference peptide method. The peak area ratio of each tryptic peptide containing the respective tyrosines of interest to the native reference peptide was measured. The percent modification of each peptide was determined based on the decrease of the amount of each peptide relative to an untreated control.
Figure 4B:
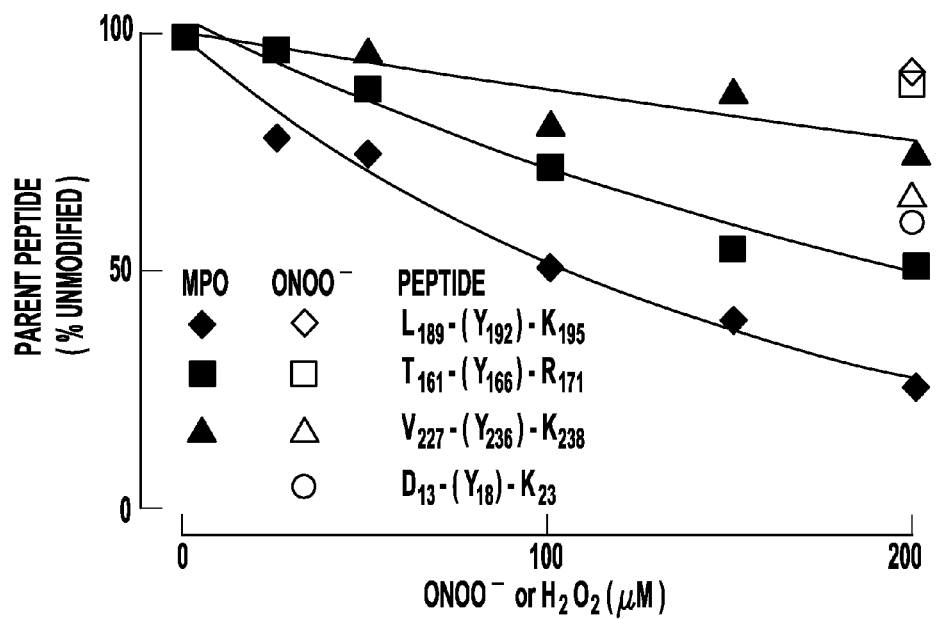
Figure 5A:
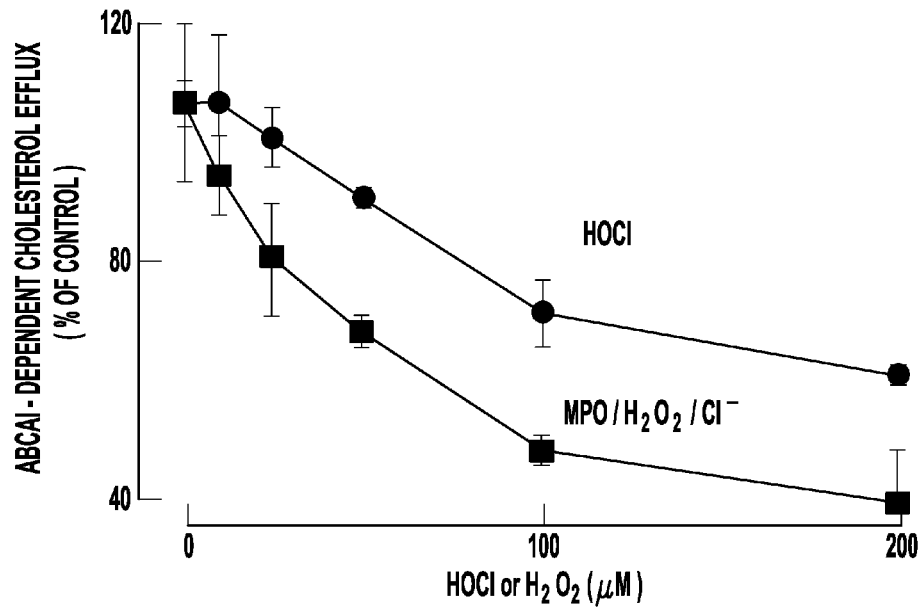
FIG. 5. Dose-dependent apoA-I chlorination and the impairment of reverse cholesterol transport activity. HDL was chlorinated in a series of either $MPO/H_2O_2/Cl^-$ reactions with increasing amounts of $H_2O_2$ or HOCl, as indicated, for 1.5 h. A) The effect of the respective chlorination reactions on the ABCA1-dependent reverse cholesterol efflux of the HDL. The efflux was determined using the same methods described in FIG. 4 for the nitration product. B) Site-specific quantitation of apoA-I chlorination determined using LC-MS. The methods used to detect and characterize these sites are given in FIG. 4.
Figure 5B:
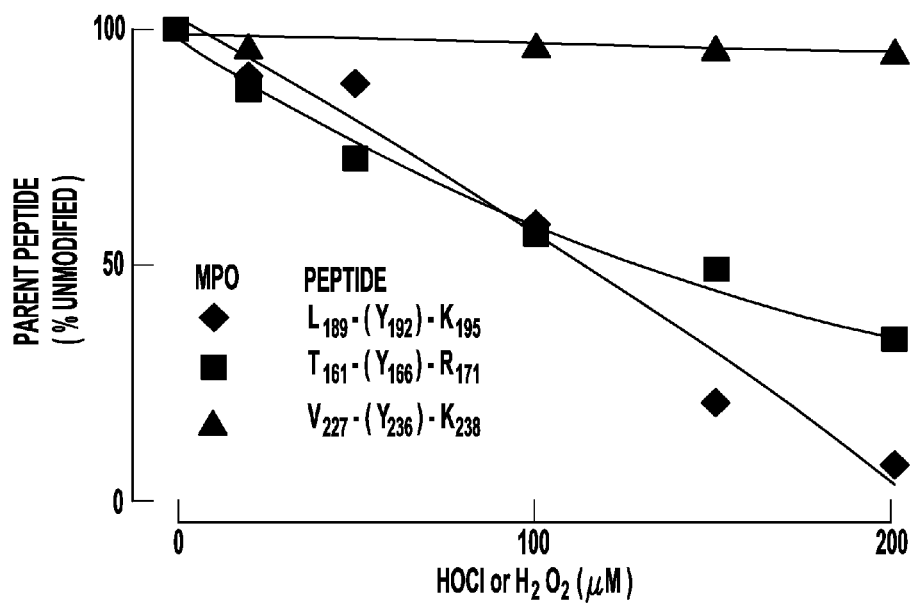
Figure 8A:
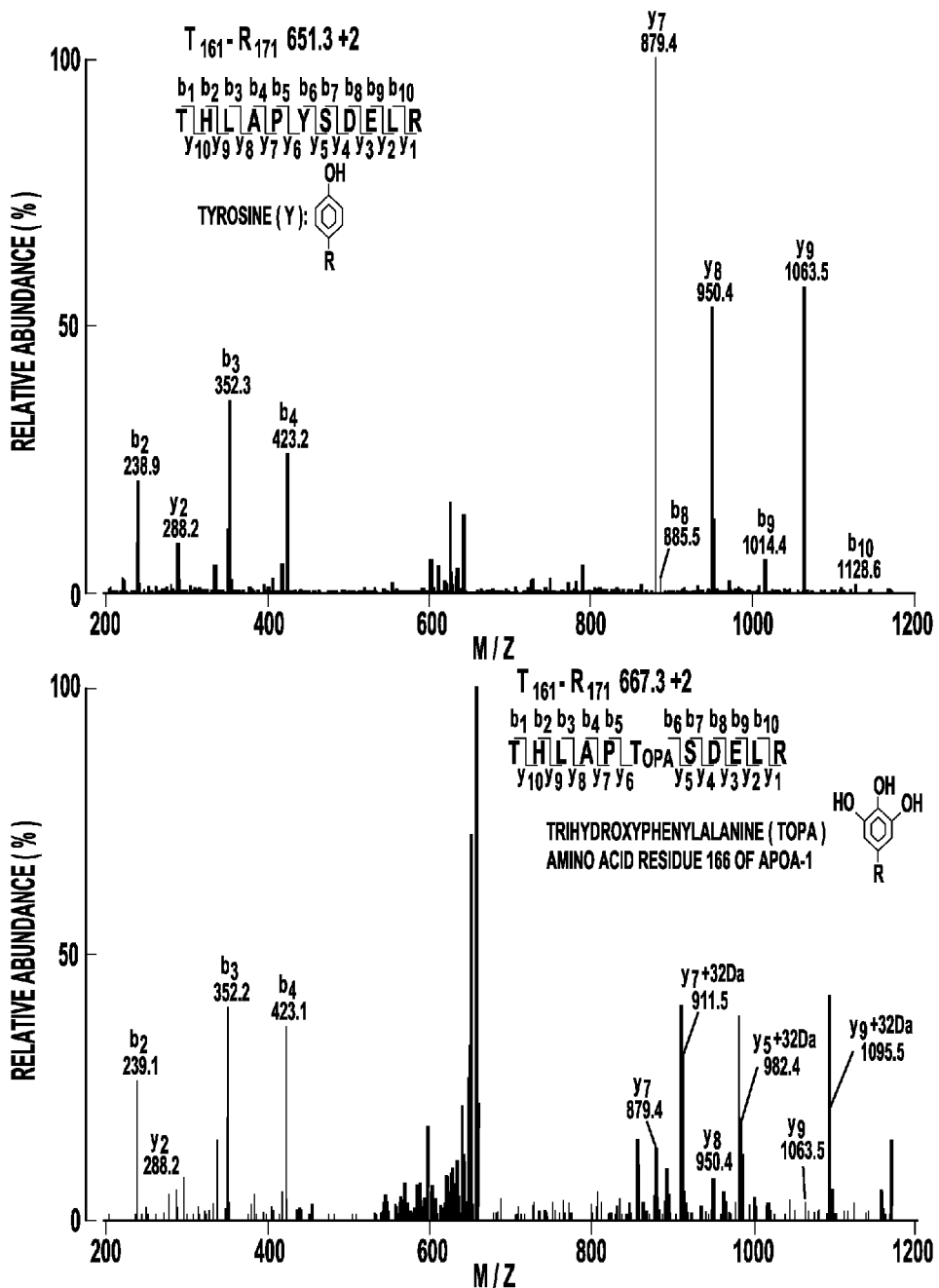
FIG. 8. Detection of nitrated peptides in apoA-I isolated from human atheroma tissue by LC-tandem mass spectrometry. Selected reaction monitoring chromatograms (SRM) for the detection, in vivo, of un-modified, oxidized peptides, after in-gel tryptic digestion of apoA-I immunoaffinity purified from human atheroma tissue. A) The CID spectrum of the oxidized peptide ($T_{161}$-$R_{171}$) of apoA-I. A residue with identical mass to trihydroxyphenylalanine (TOPA) or tyrosine hydroperoxide is detected at position 166 using CID spectrum. B) The CID spectrum of an un-modified peptide ($D_{28}$-$K_{40}$) of apoA-I. C). The CID spectrum of the oxidized peptide ($D_{28}$-$K_{40}$) of apoA-L. A residue with identical mass to TOPA or tyrosine hydroperoxide is detected at position 29, and dihydroxyphenylalanine is detected at position 33.
Figure 8B:
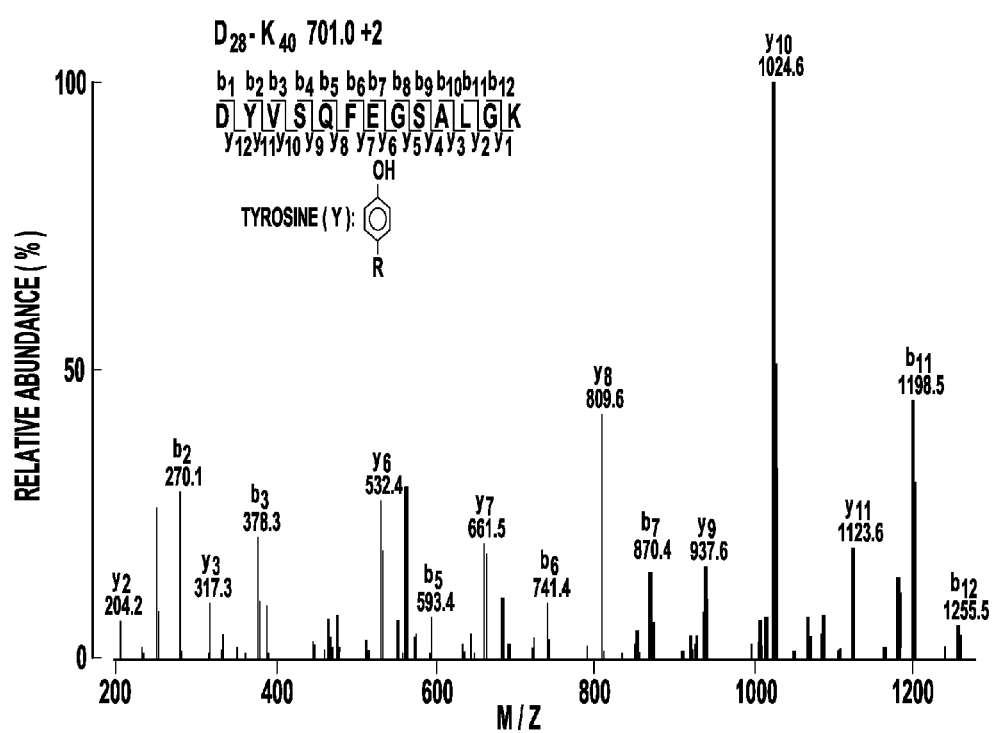
Figure 8C:
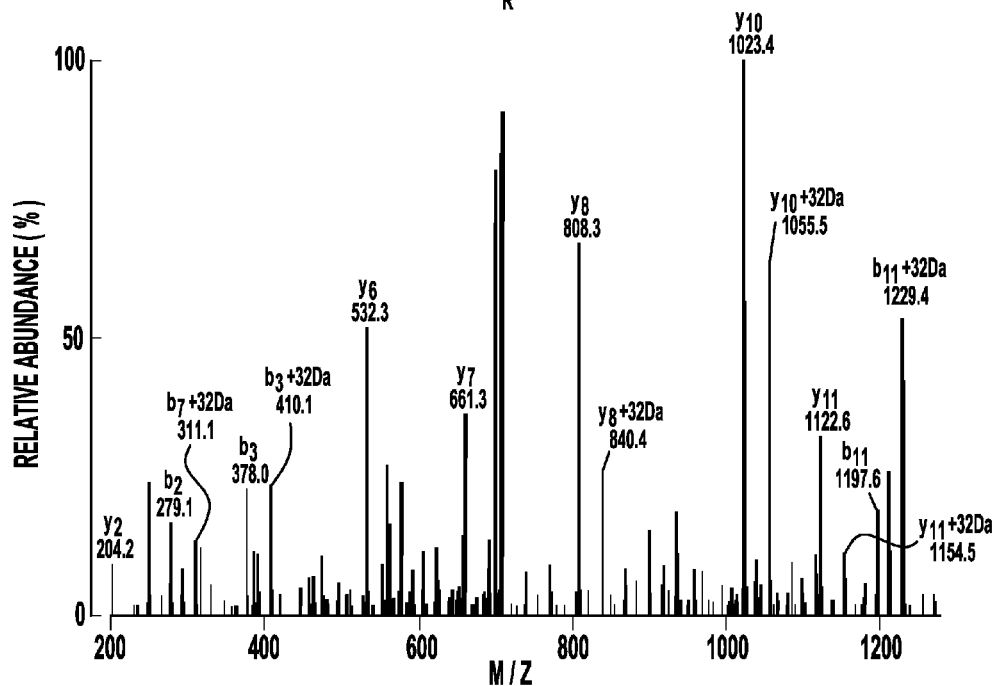

FIGS. 4A and 5A also show the dose-response effects of modification of HDL on ABCA1-mediated cholesterol efflux properties. HDL was treated with the MPO/$H_2O_2$/$NO_2^-$ system, peroxynitrite, the MPO/$H_2O_2$/$Cl^-$ system, or HOCl. Cholesterol efflux was then measured by incubation of the treated samples with cholesterol loaded murine macrophage RAW264.7 cells in the presence and absence of pretreatment with 8Br-cAMP. In the absence of 8Br-cAMP treatment, RAW264.7 cells do not express an appreciable level of ABCA1 and support ABCA1-independent cholesterol efflux to HDL but no cholesterol efflux to apoA-I (Smith, J. D., Miyata, M., Ginsberg, M., Grigaux, C., Shmookler, E., and Plump, A. S. (1996) J. Biol. Chem. 271, 30647-30655, Remaley, A. T., Stonik, J. A., Demosky, S. J., Neufeld, E. B., Bocharov, A. V., Vishnyakova, T. G., Eggerman, T. L., Patterson, A. P., Duverger, N. J., Santamarina-Fojo, S., and Brewer, H. B., Jr. (2001) Biochem. Biophys. Res. Comm. 280, 818-823, Takahashi, Y., Miyata, M., Zheng, P., Imazato, T., Horwitz, A., and Smith, J. D. (2000) Biochim. Biophys. Acta. 1492, 385-394, Chen, W., Sun, Y., Welch, C., Gorelik, A., Leventhal, A. R., Tabas, I., and Tall, A. R. (2001) J. Biol. Chem. 276, 43564-43569). 8Br-cAMP treatment of RAW264.7 cells induces ABCA1 mRNA and protein allowing 2-fold higher cholesterol efflux to HDL and significant levels of cholesterol efflux to lipid-free apoA-I (Smith, J. D., Miyata, M., Ginsberg, M., Grigaux, C., Shmookler, E., and Plump, A. S. (1996) J. Biol. Chem. 271, 30647-30655, Takahashi, Y., and Smith, J. D. (1999) Proc. Natl. Acad. Sci. U.S.A. 96, 11358-11363, Remaley, A. T., Stonik, J. A., Demosky, S. J., Neufeld, E. B., Bocharov, A. V., Vishnyakova, T. G., Eggerman, T. L., Patterson, A. P., Duverger, N. J., Santamarina-Fojo, S., and Brewer, H. B., Jr. (2001) Biochem. Biophys. Res. Comm. 280, 818-823, Takahashi, Y., Miyata, M., Zheng, P., Imazato, T., Horwitz, A., and Smith, J. D. (2000) Biochim. Biophys. Acta. 1492, 385-394). Therefore, the presence or absence of 8Br-cAMP pretreatment allows one to measure both ABCA1-dependent and -independent cholesterol efflux. As seen in FIGS. 7A and 8A, the MPO-mediated nitration and chlorination reactions, and the HOCl treatment, produced dose-dependent losses of the ABCA1-dependent cholesterol efflux to HDL without affecting ABCA1-independent efflux to HDL. Overall, the rank order of efficiency for functional impairment by various modification reactions was MPO-mediated chlorination>HOCl chlorination>MPO-mediated nitration>>peroxynitrite nitration.

Control reactions of HDL treated with $H_2O_2$ alone showed no decrease in ABCA1-dependent cholesterol efflux, demonstrating the critical nature of the MPO-catalyzed peroxidase reaction. The same tyrosine residues were also modified and a similar pattern of decreased ABCA1-dependent cholesterol efflux were seen control experiments using lipid-free apoA-I treated with the complete MPO-mediated modification systems (data not shown). These results are consistent with protein modification, as opposed to lipid modification, being responsible for the loss of efflux activity.

Figure 6A:
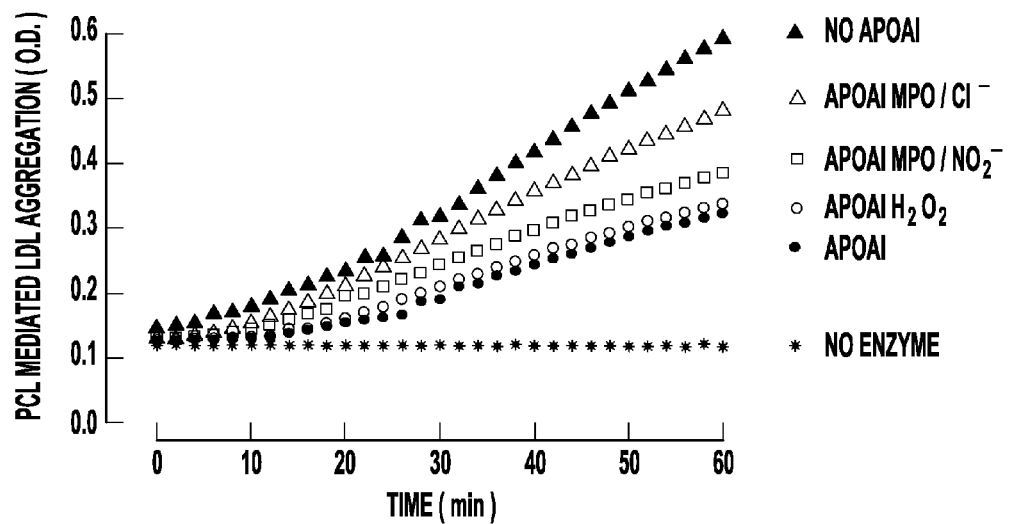
FIG. 6. ApoA-I modification inhibits lipid binding coordinately with ABCA1-dependent cholesterol acceptor activity. A) ApoA-I lipid binding activity was assayed by its ability to inhibit phospholipase C (PLC)-induced LDL aggregation over a 1 h time course at 37° C. 3 µg/ml of apoA-I or $H_2O_2$ modified apoA-I decreased LDL aggregation to approximately the same extent. Compared to unmodified apoA-I, the complete $MPO/H_2O_2/Cl^-$ modification system and to a lesser extent the $MPO/H_2O_2NO_2^-$ system led to apoA-I with decreased ability to bind to the PLC treated LDL and inhibit its aggregation. The values represent the means of triplicate wells. The ability of apoA-I to inhibit LDL aggregation was dose dependent (data not shown). B) Lipid binding was calculated from the initial slopes from the experiment shown in FIG. 6A, and normalized to the value for unmodified apoA-I (x-axis). The identical apoA-I preparations were used to assay ABCA1-dependent lipid efflux from 8Br-cAMP treated RAW264.7 in triplicate (as shown in FIG. 5B), and normalized to the value for unmodified apoA-I (y-axis). MPO modifications led to coordinate reductions in both lipid binding and ABCA1-dependent cholesterol acceptor activity (linear regression $r^2=0.96$. $p<0.0001$).
Figure 6B:
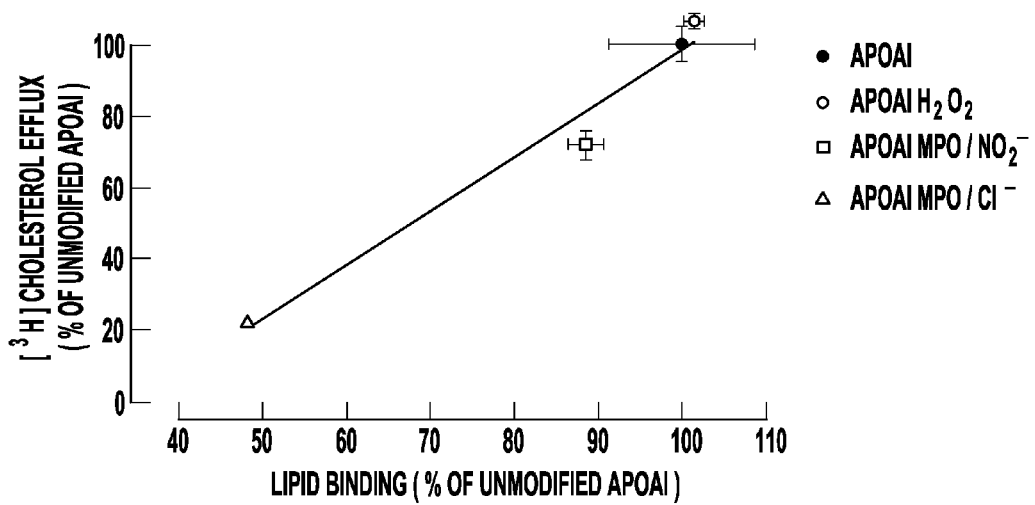
Figure 9:
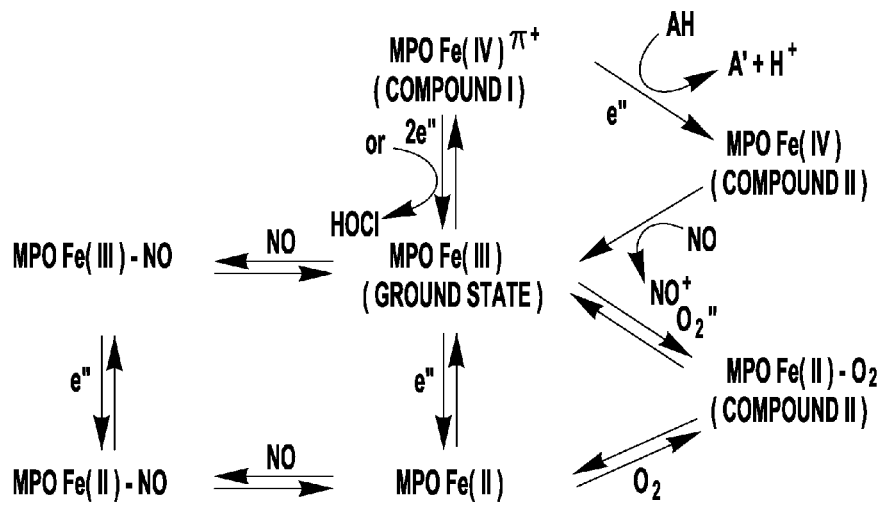
FIG. 9. A kinetic model for myeloperoxidase.

The effect of MPO-mediated modification on the lipid binding characteristics of apoA-I was also tested. These experiments measure the lipid binding activity of apoA-I by monitoring the ability of the apoA-I to inhibit the aggregation of LDL that is treated with phospholipase C (PLC). The apoA-I inhibition is due to its ability to coat the modified hydrophobic LDL through a lipid binding process that is an initial step in apoA-I-mediated cholesterol efflux. As shown in FIG. 6, LDL treated with the PLC produces a time-dependent aggregation that is significantly reduced by the lipid binding activity of unmodified apoA-I or apoA-I that was pretreated with hydrogen peroxide alone (FIG. 9A). Pretreatment of the apoA-I with the MPO-mediated nitration and chlorination systems (MPO/$H_2O_2$/$NO_2$ and MPO/$H_2O_2$/$Cl^-$, respectively) significantly inhibited this reduction with the nitration reaction giving a 10% inhibition and the chlorination reaction giving a 35% inhibition. The identical modified or control apoA-I preparations were tested for ABCA1-dependent lipid efflux acceptor activity and the decreases in apoA-I's lipid binding activity correlated directly with observed losses of ABCA1-dependent efflux acceptor activity (FIG. 9B).

Example 7

Specific apoA-I Modification Sites are Found In Vivo

Figure 10:
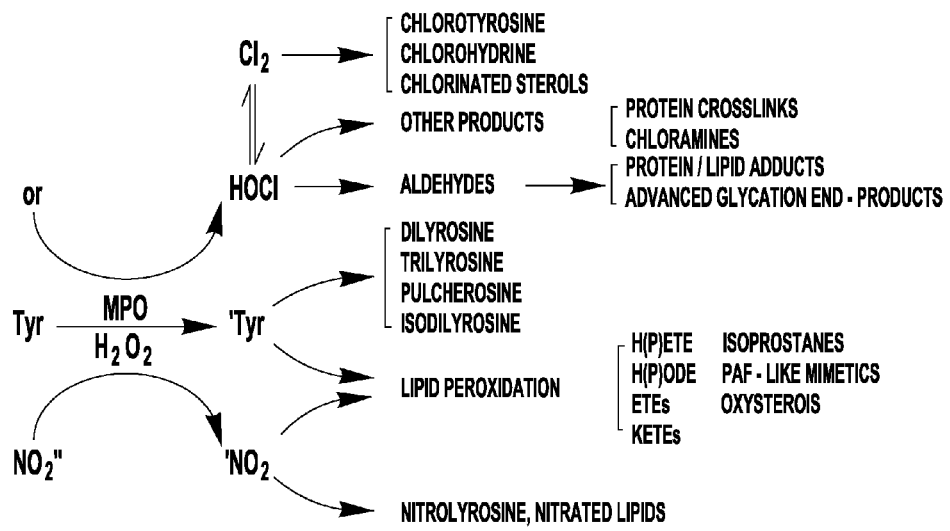
FIG. 10. A schematic representation of certain myeloperoxidase generated reactive intermediates and some MPO-generated oxidation products.

The LC-tandem MS studies of apoA-I modified in vitro by MPO, described above, produced a roster of modification sites for evaluation in vivo. FIG. 7 shows a series of SRM chromatograms from the LC-tandem MS analysis of apoA-I that was isolated from human atheroma tissues. The elution of peptides containing nitration at the two primary nitration sites, Y192 and Y166, are seen in the chromatograms shown FIGS. 7A and 7C, respectively. The CID spectra (FIGS. 10B and 10D, respectively) recorded at these retention times provide unambiguous proof of the correct identify of these nitrated peptides. The amounts of the nitrated peptides, relative to the respective un-modified peptides, can be estimated as 9% for the Y192-containing peptide and 0.2% for the Y166-containing peptide by integrating the area of each chromatographic peak. These values must be considered estimates because the relative LC-MS responses of the nitrated versus un-nitrated peptides have not been determined. Similar experiments targeting the secondary nitration sites identified through the in vitro experiments could not detect the Y29- and Y236-containing peptides in the nitrated forms (data not shown). This inability to detect these nitrated peptides is consistent with the relatively poor efficiency of the MPO-mediated nitration of these sites.

We also attempted to verify the presence of site-specific chlorinated peptides. A peptide containing chlorination at the Y192 position could not be detected (data not shown) despite the identification of this site as the preferred site of chlorination in in vitro models. The peptide containing chlorination at the Y166 position could be detected (bottom panel FIG. 7B), although the CID spectrum (bottom panel FIG. 7D) showed a superimposed spectrum of peptide ions containing chlorination of Y166 and oxidation of Y166 to give trihydroxyphenylalanine. This oxidized peptide has a molecular weight that is 2 Da lower than the corresponding chlorinated species. As a doubly charged ion, however, the chlorinated and oxidized peptides differ by 1 Da in the m/z scale of the mass spectrometer. This m/z difference cannot be distinguished in the 2 Da acceptance window of the first stage of mass analysis in the ion trap detector. The resulting singly charged fragment ions differ by 2 Da and can be distinguished in the CID spectrum.

What is claimed is:

1. A method for administering or prescribing a therapeutic agent targeting cardiovascular disease to a human patient based on an elevated level of one or more oxidized apoA-1 biomolecules comprising:
   determining, based on an assay of a biological sample from a human patient, that said human patient has elevated levels of one or more oxidized apoA-I-related biomolecules selected from oxidized apoA-1, and an oxidized apoA-I peptide fragment,
   wherein said biological sample is a blood sample, serum sample, or a plasma sample,
   wherein said oxidized apoA-1 and the oxidized apoA-1 from which said oxidized apoA-1 peptide fragments are derived, have reduced cholesterol efflux stimulating activity as compared to un-oxidized apoA-1; and
   administering or prescribing a therapeutic agent targeting cardiovascular disease to said human patient based on said elevated level of said one or more apoA-I-related oxidized biomolecules in said biological sample.

2. The method of claim 1, wherein said therapeutic agent targeting cardiovascular disease comprises a lipid lowering agent.

3. The method of claim 1, wherein the method employs a procedure or reagent for detecting oxidized apoA-I or an oxidized apoA-I peptide fragment that comprises one or more of the following amino acid residues: chlorotyrosine, nitrotyrosine, dityrosine, trihydroxy-phenylalanine, dihydroxyphenylalanine, methionine sulphoxide, and tyrosine peroxide.

4. The method of claim 1, wherein the method employs a procedure for detecting oxidized apoA-I or an oxidized apoA-I peptide that comprises an oxidized amino acid residue at any one of positions 18, 29, 166, 192, 236, or any combination of said positions, in SEQ ID NO: 1.

5. The method of claim 1, wherein levels of the one or more oxidized apoA-I related biomolecules are compared to a control value or a range of control values based upon levels of the one or more oxidized apoA-I-related biomolecules in comparable biological samples from a control population of human subjects.

6. The method of claim 1, wherein said biological sample is a plasma sample.

7. A method of prescribing a life style change to a human patient based on an elevated level of one or more oxidized apoA-1 biomolecules comprising:
   assessing, based on an assay of a biological sample from a human patient, that said human patient has an elevated level of a risk predictor selected from oxidized apoA-I, an oxidized apoA-I peptide fragment, or any combination thereof,
   wherein said biological sample is a blood sample, serum sample, or plasma sample,
   wherein said oxidized apoA-1 and the oxidized apoA-1 from which said oxidized apoA-1 peptide fragments are derived, have reduced cholesterol efflux stimulating activity as compared to un-oxidized apoA-1; and
   prescribing a life style change to said human patient based on said elevated level of said risk predictor in said biological sample.

8. The method of claim 7, wherein said biological sample is a plasma sample.

9. The method of claim 7, wherein said biological sample is a serum sample.

* * * * *